(12) United States Patent
Zhang et al.

(10) Patent No.: US 11,339,361 B2
(45) Date of Patent: May 24, 2022

(54) ADDITIVE MANUFACTURING OF FUNCTIONAL MYOCARDIAL TISSUE

(71) Applicant: The United States of America, as Represented by the Secretary of the Navy, San Diego, CA (US)

(72) Inventors: Yu Shrike Zhang, Cambridge, MA (US); Ali Khademhosseini, Los Angeles, CA (US)

(73) Assignee: United States of America as represented by the Secretary of the Navy, Washington, DC (US)

( * ) Notice: Subject to any disclaimer, the term of this patent is extended or adjusted under 35 U.S.C. 154(b) by 562 days.

(21) Appl. No.: 16/119,022

(22) Filed: Aug. 31, 2018

(65) Prior Publication Data

US 2020/0024560 A1    Jan. 23, 2020

Related U.S. Application Data

(60) Provisional application No. 62/552,878, filed on Aug. 31, 2017.

(51) Int. Cl.

| | |
|---|---|
| C12M 1/08 | (2006.01) |
| C12M 3/00 | (2006.01) |
| G01N 33/50 | (2006.01) |
| C12N 5/074 | (2010.01) |
| C12N 5/071 | (2010.01) |
| C12M 3/06 | (2006.01) |
| C12N 5/077 | (2010.01) |
| C12M 1/12 | (2006.01) |
| C12M 1/42 | (2006.01) |
| B33Y 80/00 | (2015.01) |
| B33Y 10/00 | (2015.01) |
| B33Y 70/00 | (2020.01) |

(52) U.S. Cl.
CPC ............ *C12M 21/08* (2013.01); *C12M 23/16* (2013.01); *C12M 25/14* (2013.01); *C12M 35/04* (2013.01); *C12N 5/0607* (2013.01); *C12N 5/069* (2013.01); *C12N 5/0657* (2013.01); *G01N 33/5061* (2013.01); *G01N 33/5064* (2013.01); *G01N 33/5088* (2013.01); *B33Y 10/00* (2014.12); *B33Y 70/00* (2014.12); *B33Y 80/00* (2014.12)

(58) Field of Classification Search
CPC ...... C12M 21/08; C12M 25/14; C12M 23/16; C12M 29/10; C12M 35/04; G01N 33/5061; G01N 33/5064; G01N 33/5088; C12N 5/0607; C12N 5/069; C12N 5/0657; C12N 2535/00; C12N 2533/74; C12N 2533/54; C12N 2533/30; C12N 5/0697; C12N 2502/1329; C12N 2503/04; C12N 2503/02; C12N 2513/00; C12N 2502/28; C12N 2506/45; B33Y 80/00; B33Y 10/00; B33Y 70/00; B29C 64/106

See application file for complete search history.

(56) References Cited

FOREIGN PATENT DOCUMENTS

WO    WO-2017090777 A1 * 6/2017    ............. A61L 27/38

OTHER PUBLICATIONS

Hsieh et al. "Gradient static-strain stimulation in a microfluidic chip for 3D cellular alignment." Lab on a Chip, Jan. 31, 2014, 14(3): 482-493 (Year: 2014).*
Weinberger et al. "Cardiac repair in guinea pigs with human engineered heart tissue from induced pluripotent stem cells." Science Translational Medicine Nov. 2, 2016: (Year: 2016).*
Pati et al. "Printing three-dimensional tissue analogues with decellularized extracellular matrix bioink." Nat Commun . Jun. 2, 2014;5:3935. (Year: 2014).*
Muller-Ehmsen et al. "Long-Term Survival of Transplanted Neonatal Rat Cardiomyocytes After Myocardial Infarction and Effect on Cardiac Function." Circulation . Apr. 9, 2002;105(14):1720-6. (Year: 2002).*
Sobral et al. "Three-dimensional plotted scaffolds with controlled pore size gradients: Effect of scaffold geometry on mechanical performance and cell seeding efficiency." Acta Biomater .Mar. 2011;7(3):1009-18. (Year: 2011).*
Jia et al. "Direct 3D bioprinting of perfusable vascular constructs using a blend bioink." Biomaterials. Nov. 2016; 106: 58-68 (Year: 2016).*
Kim SB et al., A Cell-Based Biosensor For Real-Time Detection of Cardiotoxicity Using Lensfree Imaging. Lab Chip. 2011;11:1801-7.
Iyer RK et al., Vascular Endothelial Growth Factor Secretion by Nonmyocytes Modulates Connexin-43 Levels in Cardiac Organoids. Tissue Eng A. 2012;18:1771-83.
Colosi C et al., Microfluidic Bioprinting of Heterogeneous 3D Tissue Constructs Using Low Viscosity Bioink. Adv Mater. 2015;28:677-84.

(Continued)

*Primary Examiner* — Titilayo Moloye
(74) *Attorney, Agent, or Firm* — Naval Information Warfare Center, Pacific; Kyle Eppele; James McGee

(57) ABSTRACT

A bioreactor and methods for use can include a microfibrous scaffold, that can be made of a composite bioink, and that can have endothelial cells directly embedded within the scaffold using an additive manufacturing process. The scaffold can further be seeded with cardiomyocytes. The hydrogel scaffold can be composed of a plurality of serpentine layers, with each serpentine layers, which can be placed on each other in a cross-hatch configuration, so that the primary axes of successive layers are perpendicular. This configuration can establish an aspect ratio for the scaffold, which can be selectively varied. For greater strength, the successive layers that have a primary axis in the same direction can be placed in the scaffold so that they are slight offset from each other. The scaffold can be placed in the bioreactor with perfusion, for use in cardiovascular drug screening and other nanomedicine endeavors.

20 Claims, 23 Drawing Sheets

(56) References Cited

OTHER PUBLICATIONS

Zhang YS et al., A Cost-Effective Fluorescence Mini-Microscope for Biomedical Applications. Lab Chip. 2015;15:3661-9.

Merkel TC et al., Gas Sorption, Diffusion, and Permeation in Poly (Dimethylsiloxane). J Polym Sci, Part B: Polym Phys. 2000;38:415-34.

Abaci HE et al., Unforeseen Decreases In Dissolved Oxygen Levels Affect Tube Formation Kinetics In Collagen Gels. American Journal of Physiology—Cell Physiology. 2011;301:C431-C40.

Radisic M et al., Mathematical Model of Oxygen Distribution in Engineered Cardiac Tissue with Parallel Channel Array Perfused With Culture Medium Containing Oxygen Carriers. American Journal of Physiology—Heart and Circulatory Physiology. 2005;288:H1278-H89.

Bhise NS et al., A Liver-on-a-Chip Platform with Bioprinted Hepatic Spheroids, Biofabrication. 2016;8:014101.

Annabi N et al., Highly elastic micropatterned hydrogel for engineering functional cardiac tissue. Adv Funct Mater. 2013;23:4950-9.

Bae H et al., Building Vascular Networks. Sci Transl Med. 2012;4:160ps23-ps23.

Kaemmerer E et al., Gelatine methacrylamide-based hydrogels: An alternative three-dimensional cancer cell culture system. Acta Biomater. 2014;10:2551-62.

Wikswo JP et al., Scaling and systems biology for integrating multiple organs-on-a-chip. Lab Chip. 2013;13:3496-511.

Lin R-Z, Transdermal regulation of vascular network bioengineering using a photopolymerizable methacrylated gelatin hydrogel. Biomaterials 2013;34:6785-96.

Lee VK, Kim DY, Ngo H, Lee Y, Seo L, Yoo S-S, et al. Creating perfused functional vascular channels using 3D bio-printing technology. Biomaterials 2014;35:8092-102.

Wu W, DeConinck A, Lewis JA. Omnidirectional Printing of 3D Microvascular Networks. Adv Mater. 2011;23:H178-H83.

Zhang, Y.S. et al., Multisensor-Integrated Organs-on-Chips Platform for Automated and Continual in situ Monitoring of Organoid Behaviors, www.pnas.org/cgi/doi/10.1073/pnas.1612906114 PNAS | Published online Mar. 6, 2017 | E2293-E2302.

Zhang, Y.S. et al.. Bioprinting 3D Microfibrous Scaffolds for Engineering Endothelialized Myocardium and Heart-on-a-Chip, Biomaterials 110 (2016) 45-59, http://dx.doi.org/10.1016/j.biomaterials.2016.09.003.

* cited by examiner

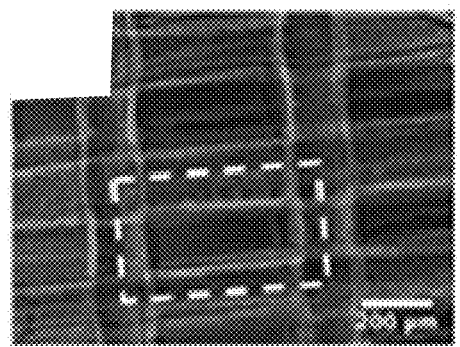
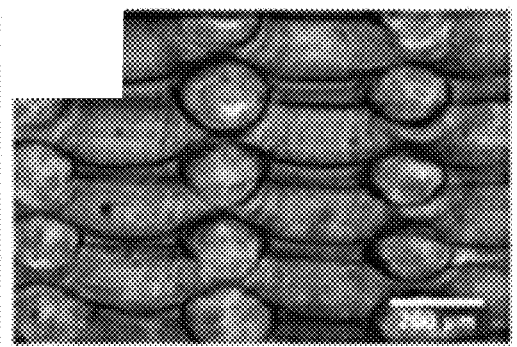
FIG. 3K  FIG. 3L
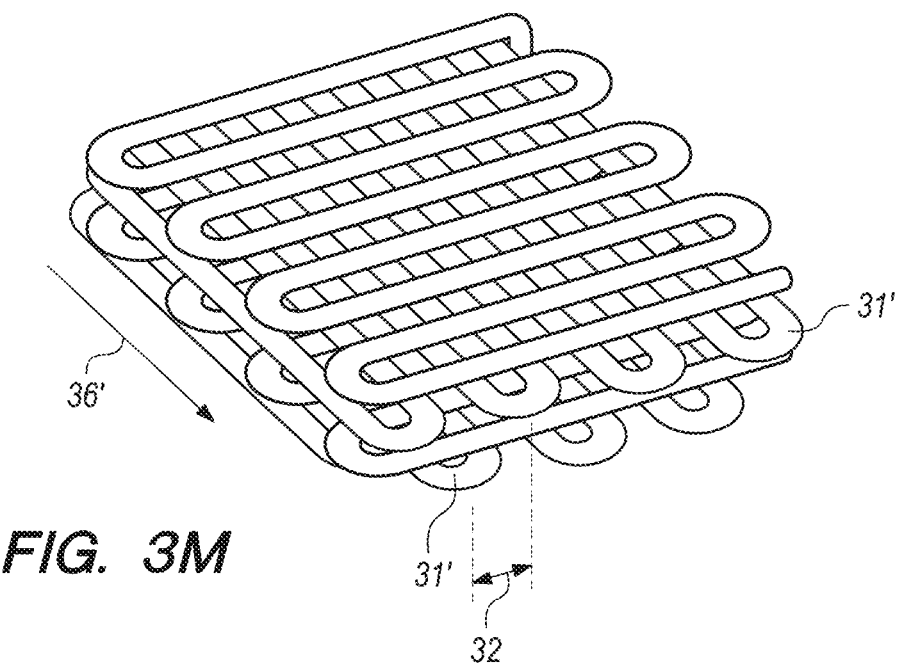
FIG. 3M

ADDITIVE MANUFACTURING OF FUNCTIONAL MYOCARDIAL TISSUE

CROSS REFERENCE TO RELATED APPLICATIONS

This application claims the benefit of U.S. Provisional Application 62/552,878, filed Aug. 31, 2017, by Yu Shrike Zhang et al., entitled "Additive Manufacturing of Functional Myocardial Tissue". The contents of the '878 application are hereby incorporated by reference into this specification.

FEDERALLY SPONSORED RESEARCH AND DEVELOPMENT

The United States Government has ownership rights in this invention, pursuant to passing of title to a Subject Invention under Government Contract N66001-13-C-2027 (Wake Forest University). Licensing inquiries may be directed to Office of Research and Technical Applications, Space and Naval Warfare Systems Center, Pacific, Code 72120, San Diego, Calif., 92152; telephone (619) 553-5118; email: ssc_pac_t2@navy.mil, referencing 105804.

FIELD OF THE INVENTION

The present invention pertains generally to additive manufacturing systems and methods. More specifically, the present invention can pertain to systems and methods for additive manufacturing of cardiac tissues and organ models. The present invention can be particularly, but not exclusively, useful as systems and methods for additive manufacturing of cardiac tissues and organ models that can seed a three dimensional endothelial bed with cardiomyocytes using a controlled anisotropy, in order to generate aligned myocardium capable of spontaneous and synchronous contraction.

BACKGROUND OF THE INVENTION

Engineering cardiac tissues poses a series of critical challenges that need to be addressed in order to translate basic research products from bench to clinical practice. The engineered cardiac organoids coupled with microfluidic bioreactors (e.g. heart-on-chips) have also found increasing applications in functioning as enabling in vitro biomimetic models to study pathology, measure cardiotoxicity, and develop new therapeutics. One of the first challenges in engineering cardiac organoids and their on-chip forms in the prior art can be the fact that mature cardiomyocytes exhibit limited self-renewing potential. In this framework, induced pluripotent stem cells (iPSCs) hold great promise, due to their wide availability and the possibility to differentiate into multiple cell lineages including cardiomyocytes. Second, the alignment of cardiomyocytes and their organization into bundles characterized by spontaneous and synchronous contraction further complicate the development of biologically relevant cardiac tissues. Third, the generation of thick (cardiac) tissue constructs requires the introduction of microvascular networks in order to provide oxygen and nutrients, remove waste products, and eventually promote vessel anastomosis with the host vasculature.

Several approaches have so far been explored in the prior art to generate functional tissue constructs including the myocardium. For example, scaffold-free multicellular cardiac spheroids have been developed that could spontaneously and synchronously contract. While the cardiac spheroids have served an important role in drug testing and have been widely used due to the ease of preparation, these constructs can lack the directionality characterized by the physiological myocardium, which can be critical to maintain the long-term functionality of the engineered cardiac tissues.

On the other hand, prior art scaffold-based techniques can provide an ideal support for cell adhesion, distribution, and responses. Importantly, the architecture of the scaffolds can be conveniently modulated in order to promote the biological relevance of the engineered tissues by tuning spatial organizations that mimic in vivo counterparts. For example, it has been demonstrated that anisotropic scaffolds bearing an accordion-like honeycomb structure could induce the generation of highly oriented cardiac fibers. Biowire approaches to induce the differentiation and alignment of the cardiomyocytes from human pluripotent stem cells have also been discussed in the literature. Still further, it has been shown that cardiac tissues can be populated with microfilament arrays seeded with cardiomyocytes to engineer aligned cardiac tissues; hydrogel substrates with aligned ridges/grooves via photopatterning to improve the adhesion and alignment of cardiomyocytes have recently been developed. Other strategies have further been investigated to integrate blood vessels into engineered tissues including the myocardium. However, generating volumetric cardiac tissues containing embedded endothelial networks remains challenging.

Bioprinting has recently emerged as a promising technology to produce geometrically defined structures in three dimensions (3D), significantly improving their physiological relevance through architectural mimicry of native tissues and organs. Particularly, bioprinting overcomes major drawbacks of conventional scaffold-based approaches including limited control over the 3D structures of engineered tissues and thus reduced reproducibility. Additionally, the bioprinting process is usually biocompatible, allowing for direct encapsulation of bioactive molecules and cells. Still further, bioprinting may enable vascularization of the engineered tissue constructs based on sacrificial methods or direct deposition, providing additional versatility in producing vascularized cardiac organoids.

In view of the above, it can be an object of the present invention to provide systems and methods for additive manufacturing of myocardial tissue that can yield functional cardiac tissue that is capable of contraction. Still another object of the present invention can be to provide systems and methods for additive manufacturing of myocardial tissue that can yield functional cardiac tissue for use in regenerative medicine, drug screening, and potentially disease modeling application. Yet another object of the present invention can be to provide systems and methods for additive manufacturing of myocardial tissue that can yield functional tissue, which can further yield the perfusion of such an endothelialized network in the future upon usage of sacrificial bioinks that can be removed, to enhance the biomimetic properties of produced vascularized organoids. Another object of the present invention can be to provide systems and methods for additive manufacturing of myocardial tissue that can eventually be somewhat easy to use in a cost-efficient manner.

SUMMARY OF THE INVENTION

A bioreactor and methods for using said bioreactor for drug screening, can include a microfibrous hydrogel scaffold, that can be made of a composite alginate-gelatin methacryloyl (GelMA) bioink, and that can have endothelial cells directly embedded within the scaffold. The scaffold can further be seeded with cardiomyocytes so that said bioreactor has a controlled anisotropy, and the scaffold can be placed in a chamber defined by a PDMS half pieces, that compress the scaffold slightly when the PDMS half pieces are fastened to each other. The chamber could certainly be made of other materials as chosen by the end user, including but not limited to, thermoplastics, glass, etc.

The hydrogel scaffold can be composed of a plurality of serpentine layers, with each serpentine layer having a primary axis defined by the serpentine layer tines. Successive serpentine layers can be placed on each other in a crosshatch configuration, so that the primary axes of successive layers are perpendicular. This configuration can establish a plurality of rectangular holes that have an aspect ratio when viewed in plan view. The aspect ratio can vary from 2×2, 2×3, 2×4, and 2×5. The successive layers that have a primary axis in the same direction can be placed in the scaffold so that they are offset from each other. The microfibrous hydrogel scaffold can be manufactured using additive manufacturing techniques.

In some embodiments, the cardiomyocytes can be neonatal rat cardiomyocytes. In still other embodiments, cardiomyocytes can be human induced pluripotent stem cell (hiPSC)-derived cardiomyocytes, and in particular hiPSC-derived cardiomyocytes from the candidate patient for whom the drug screening process is being accomplished.

BRIEF DESCRIPTION OF THE DRAWINGS

The novel features of the present invention will be best understood from the accompanying drawings, taken in conjunction with the accompanying description, in which similarly-referenced characters refer to similarly-referenced parts, and in which:

FIG. 3K can be a top plan micrograph of the scaffold of FIG. 3A;

FIG. 3L can be a cross-sectional micrograph of the scaffold of FIG. 3A

FIG. 3M can be the same view as FIG. 3A, but with the microfibrous scaffold layers having an offset;

FIG. 3N can be top plan micrograph of the scaffold of FIG. 3M;

FIG. 3O can be a cross-sectional micrograph of the scaffold of FIG. 3M;

DETAILED DESCRIPTION OF THE EMBODIMENTS

Figure 1A:
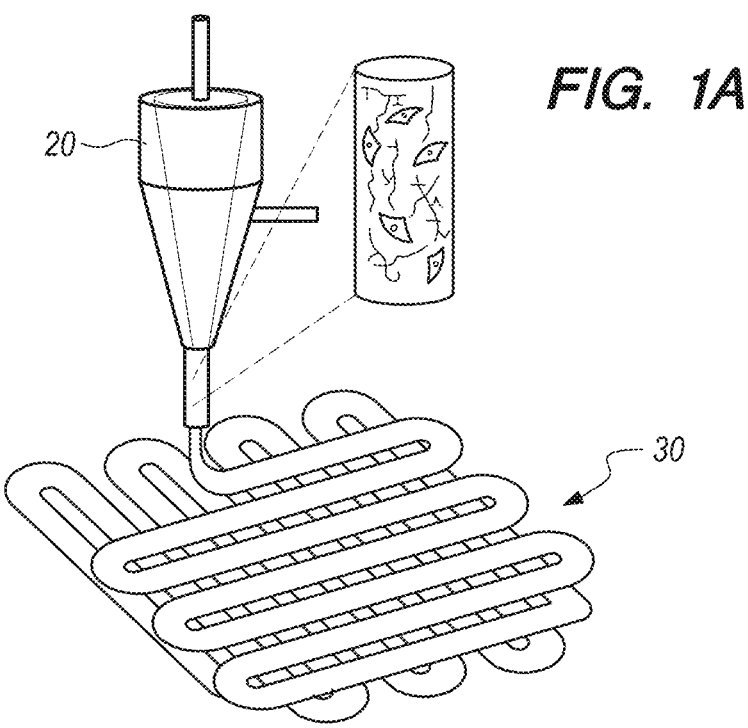
FIG. 1A can be a pictorial depiction of the microfibrous scaffold resulting from the bioprinting step of the methods of the present invention.
Figure 1B:
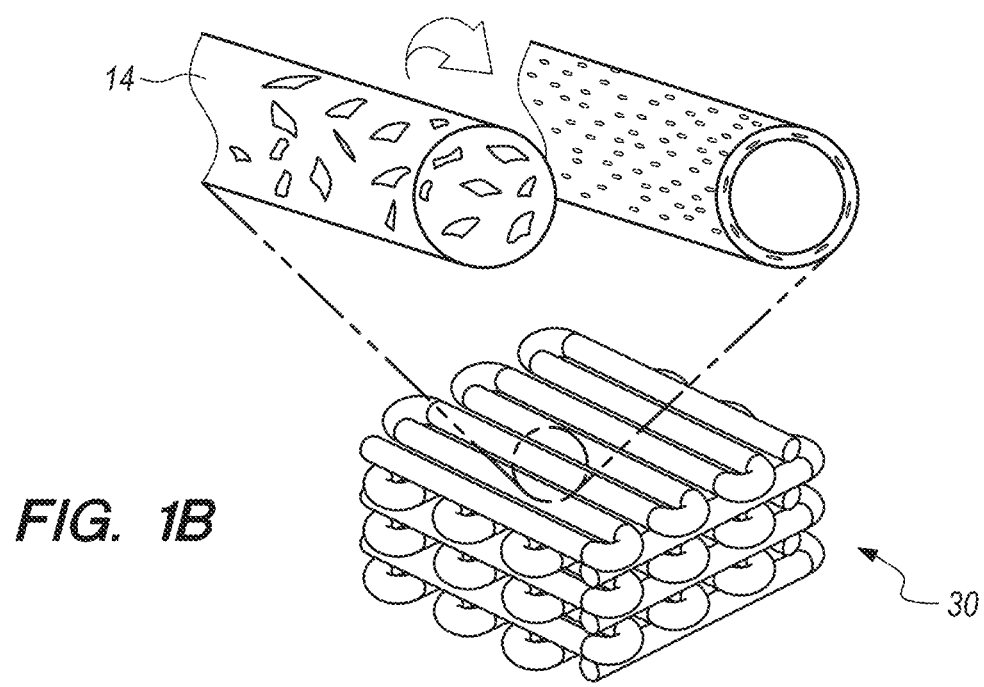
FIG. 1B can be a pictorial depiction of the formation of a vascular bed resulting from the microfibrous scaffold of FIG. 1A.
Figure 1C:
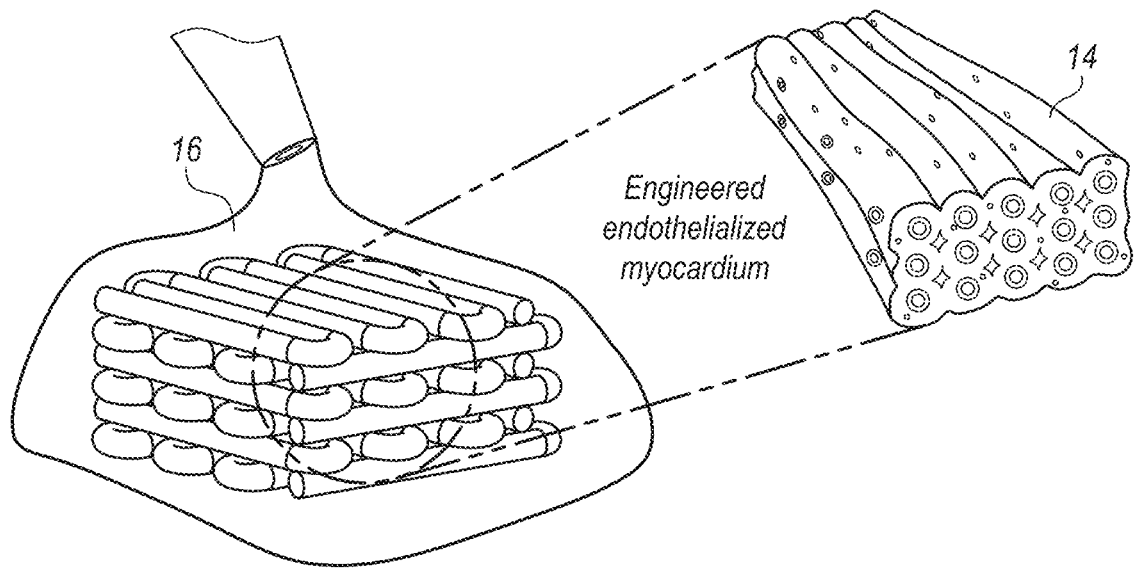
FIG. 1C can be a pictorial depiction of the vascular bed of FIG. 1B being seeded with cardiomyocytes.
Figure 1D:
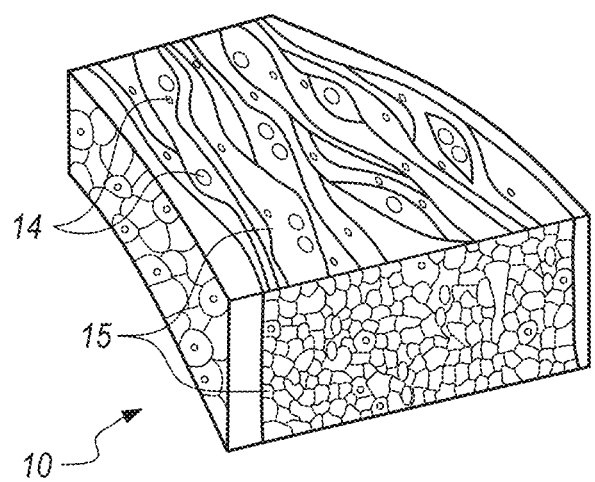
FIG. 1D can be a depiction of engineered endothelialized myocardium resulting from FIG. 1C, FIG. 2A can be an enlarged view of the coaxial needle portion of a bioprinter which can be used to accomplish the systems methods of the present invention according to several embodiments.

In brief overview, and referring initially to FIGS. 1A-1C, in this work a novel hybrid strategy based on 3D bioprinting can be presented (as used in this Specification, "bioprinting", "3D bioprinting" and "additive manufacturing" can be taken to mean the same thing), to engineer endothelialized myocardial tissue 10 (FIG. 1D). Based on the microfluidic technology that has been developed in the prior art, it can be demonstrated that endothelial cells 11 can be directly encapsulated within the bioprinted microfibrous scaffold 30, as shown in FIG. 1A. The cells can gradually migrate towards the peripheries of the microfibers to form a layer of confluent endothelium. Such assembly of the endothelial cells 11 can resemble a blood vessel structure 14 (see FIGS. 1B-1C). The assembly can be enabled by the use of composite alginate-GelMA bioink with a dual-step crosslinking process, and can be potentially facilitated by the intrinsic polarization tendency of these cells as well as presence of a nutrient gradient across the diameter of the microfibers.

In contrast with the prior art, however, this 3D bioprinted endothelialized microfibrous scaffold of the present invention according to several embodiments, together with precisely controlled macroscale anisotropic architecture of the microfibers, can be seeded with cardiomyocytes 15 (See FIG. 1D) to induce the formation of myocardium with improved alignment capable of spontaneous and synchronous contraction. When further combined with a specially designed microfluidic perfusion bioreactor, the resulting endothelialized-myocardium-on-a-chip platform could be adopted to screen pharmaceutical compounds for their cardiovascular toxicity. Finally, it can be demonstrated that such a model could be easily translated to hiPSC-derived cardiomyocytes to construct endothelialized human myocardium and their on-chip forms that are responsive to drugs for testing and/or screening purposes.

2. Materials and Methods 2.1. Cell Culture

HUVECs and GFP-labeled HUVECs were obtained from LONZA® and cultured in endothelial growth medium (EGM, LONZA®). Neonatal rat cardiomyocytes were isolated from 2-day-old Sprague-Dawley rats following the established protocol approved by the Institutional Animal Care and Use Committee at the BRIGHAM AND WOMEN'S HOSPITAL® of Boston, Mass. The cells can then be maintained in Dulbecco's modified Eagle medium (DMEM) by GIBCO®, supplemented with 10 volume % fetal bovine serum (FBS) and 1 volume % penicillin-streptomycin (P-S, all from THERMO FISHER®). hiPSC-derived cardiomyocytes can be purchased from STEM CELL THERANOSTICS® and maintained in RPMI-1640 medium containing 1×B27 supplement (provided by THERMO FISHER®). It should be appreciated that many of the above components used for the cell culture are readily available commercial components. Other components could certainly be used to practice the systems and methods of the present invention.

2.2. Bioprinting Process

Figure 2A:
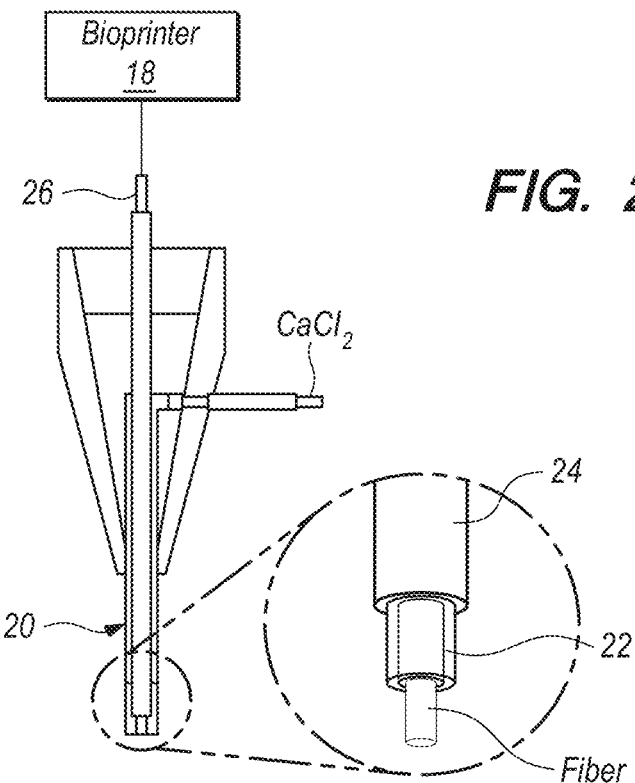
FIG. 2B can be a representation of the first step crosslink of the alginate component shown in FIG. 1C by $CaCl_2$.
FIG. 2C can be a representation of the second step crosslink of the component of FIG. 2B with a composite alginate-gelatin methacryloyl (GeIMA) GeIMA component.
FIG. 2D can be a color photograph of a representative bioprinted cubic scaffold resulting from FIG. 2C, beside a penny for reference.
FIG. 2E can be a graph of estimated printability and non-printability for different concentrations of GeIMA-high methacryloly substitution (HM) and GeIMA-low methacryloly substitution (LM)

Referring now to FIG. 2A, a bioprinter 18 can be shown. For the methods of the present invention, a bioprinter 18 can be used in combination with a custom-made coaxial nozzle extruder 20, which can further be assembled from inner and outer syringe needles 22, 24, that can be arranged so that the needles 22, 24 can be concentric to each other, as can be seen in FIG. 2A. More specifically, an 18G outer needle 24 (OD:1270 µm; ID:840 µm) can be used as the sheath and a 27G inner needle 22 (OD:410 µm; ID:210 µm) can constitute the core. The needles 22, 24 can be connected to a syringe pump (not shown in FIG. 2A) for injection of the bioink 26 and the CaCl$_2$ solution through two polyvinyl chloride) (PVC) tubes (Cole-Parmer). All the junctions can be permanently fixed using epoxy glue. The extruder 20 can be mounted onto the pump head of the bioprinter by an in-house fabricated L-shaped plastic holder 28 that can be made of poly (methyl methacrylate) (PMMA).

The bioink 26 used for the bioprinting for the systems and methods of the present invention can consist of a mixture of alginate, GelMA (SIGMA-ALDRICH®), and photoinitiator IRGACURE® 2959 (Ciba Specialty Chemicals) dissolved in 25 mM 2-[4-(2-hydroxyethyl) piperazin-1-yl] ethane sulfonic acid (HEPES) buffer, pH 7.4, SIGMA-ALDRICH®) containing 10% FBS by volume. The composition of the bioink can enable a dual-step crosslinking procedure. During the bioprinting process the ionic crosslink of the alginate component of the bioink delivered through the core of the nozzle was first induced by exposing the extruded microfibers to a 0.3M CaCl$_2$ solution in HEPES buffer containing 10 volume % FBS, carried by the sheath (outer needle 24). When the scaffold was printed, a stable gelation can be achieved by crosslinking GelMA via ultraviolet (UV) exposure. For example, a sample can be placed 7 cm away from the UV source (One device that could be used is an 800 mW source manufactured by OMNICURE®) and cross-linked for 30 seconds. In order to ensure continuous production of scaffolds avoiding clogging during the bioprinting, the composition of the bioink can be optimized by maintaining the concentration of alginate constant at 4 weight by volume percent (w/v %) while varying the relative concentrations of GelMA-LM and GelMA-HM.

For the systems and methods of the present invention, a processor can be connected to bioprinter 18, and written instructions can in input into the processors to cause the bioprinter 18 to deposit structures with a particular size and geometry. For example, MATHWORKS® code by MATLAB® can be written to automatically generate G-code to control the bioprinter to deposit desired structures. Still further, microfibrous scaffolds with a dimension of 5.5×3.5×0.75 mm$^3$ can be bioprinted through continuous deposition of one single continuous microfiber shaped in 3D for each scaffold. Printing can be performed by using the same flow rate of 5 µL/min for both the bioink and the crosslinking solution and a deposition speed of 4 mm/s. The structure of the microfibrous scaffolds is described more specifically below.

2.3. Mechanical Characterization of the Bioprinted Scaffolds

Compressive stress-strain measurements were performed to evaluate the elastic moduli of the scaffolds. The samples were bioprinted and allowed to swell for 6 h in PBS. The scaffolds were loaded onto an INSTRON® 5943 equipped with a 10-N load cell. The compressions were carried out at a strain rate of 1 mm/min to 70% deformation, at room temperature. Elastic moduli of the scaffolds were derived from the regression of the first linear portion of the stress-strain curves (whereas the second linear portion relates to the property of the cross-linked bioink after compression of all the pores). Each measurement was performed in quintuplicate.

2.4. Bioprinting of HUVECs and Seeding of Cardiomyocytes

Both bioink 26 and CaCl$_2$ solutions can be maintained at 37° C. before use. HUVECs can be re-suspended in the bioink at a concentration of 1×10$^7$ cells/mL. Following the bioprinting and the subsequent crosslinking processes, the constructs can be washed with PBS to remove excess CaCl$_2$. After washing, the constructs can be cultured in endothelial cell growth medium (EGM) at 37° C. and 5% CO$_2$ volume throughout a period of up to 33 days. The EGM/CO$_2$ medium can be changed twice in the first day and then every 2 days thereafter.

For testing of the systems and methods according to several embodiments, neonatal rat cardiomyocytes were seeded following the formation of a layer of confluent endothelium at the peripheries the microfibers of the scaffolds, which generally occurred in 15 days. Freshly isolated cardiomyocytes were suspended in DMEM at a final concentration of 1×10$^6$ cells m/L. The scaffolds were individually placed on top of a thin layer of hydrophobic polydimethylsiloxane (PDMS). Approximately 40 µL of cell suspension was dropped to cover each scaffold, and incubated at 37° C. for 2 hours, to allow the cardiomyocytes to adhere onto the microfibers. The scaffolds were then gently washed and cultured in DMEM supplemented with 10 vol.

% FBS. The medium was changed every day in the first 2-3 days until the cardiomyocytes started beating, after which only half of the medium can be exchanged every 2 to 3 days.

The seeding of hiPSC-cardiomyocytes can follow the same procedure that is described above for neonatal rat cardiomyocytes, except that a Roswell Park Memorial Institute (RPMI)-1640 medium containing 1×B27 supplements (by GIBCO®) can be used for culturing. Other choices in the prior art that are known for culturing cardiomyocytes might also be possible.

2.5. Bioreactor Design and Fabrication

Referring now to FIGS. 6A-6D, a microfluidic bioreactor 60 can be designed, optimized, and fabricated in order to construct an endothelialized-heart-on-a-chip device and for the study of drug effects. The designed bioreactor 60 according to several embodiments, can include two hemi-chambers 68a, 68b that can define a chamber for receiving the scaffold 30. The hemi-chambers 68 can including a pair of rigid supports 62a, 62b that can be made of PMMA and two complementary micro-featured gaskets 64a, 64b made of PDMS. A layer 65 of glass can optionally be included. Both PMMA layers can have a rectangular (5×3.5×0.3 cm$^3$) volume, and can further be formed with four clearance holes 66. These holes 66 can allow for the mechanical compression of the PDMS gaskets 64 (collectively have a gasket volume of 3×1.8×0.3 cm$^3$) to be sandwiched in between the support and compressed through the use of four sets of screws and nuts to guarantee hydraulic tightness and microfluidic integrity. The two micro-featured PDMS layers together can result in a bioreactor chamber 68 (FIG. 6C) with a resulting thickness of 1 mm (which reduced to approximately 0.85 mm upon compression). Tubes 69 can be connected to the inlet and outlets of chamber 68 to provide blood flow through chamber 68 (and scaffold 30 when installed).

Figure 6A:
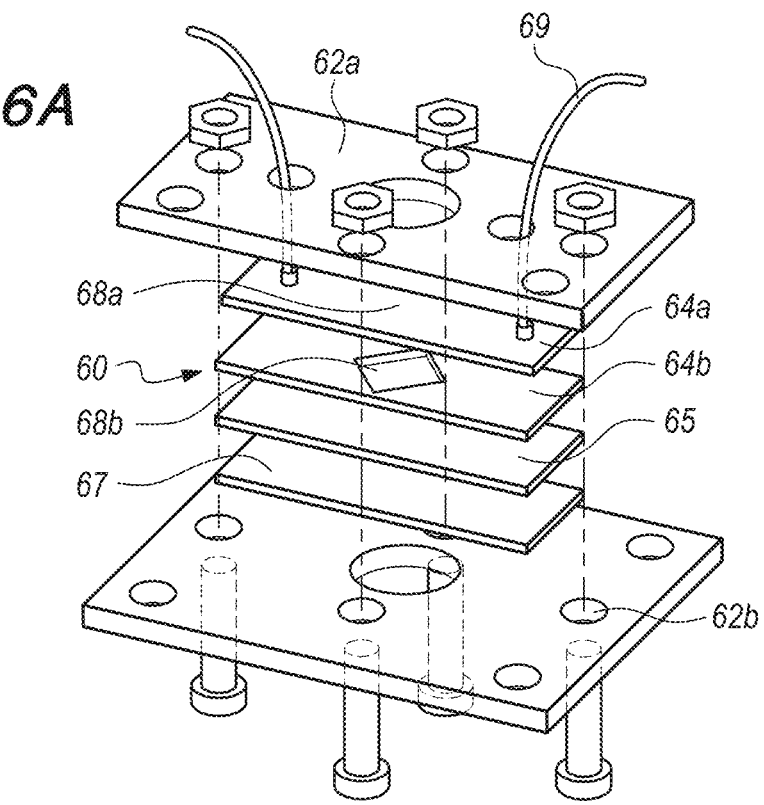
FIG. 6A can be an exploded elevational view of the two-layer microfluidic bioreactor for the screening device of the present invention according to several embodiments.
Figure 6B:
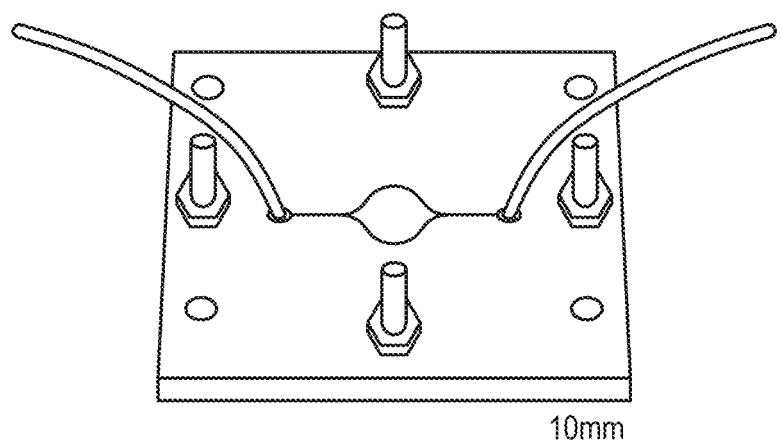
FIG. 6B can be a photograph of the device of FIG. 6A, with an embedded bioprinted scaffold.
Figure 6C:
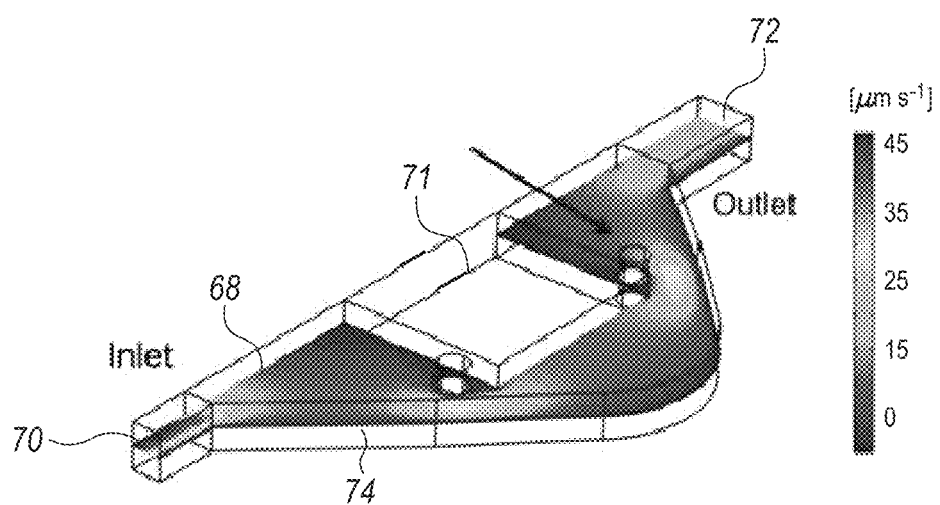
FIG. 6C can be a depiction of simulation results of flow velocity and oxygen distribution in the bioreactor chamber at a flow rate of 50 µL/min.
Figure 6D:
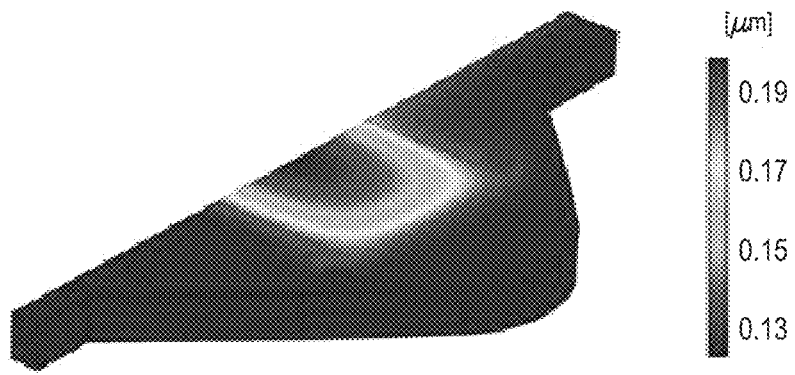
FIG. 6D can be the same depiction as FIG. 6C, but in units of µM.

As shown in FIG. 6C-6D, the main chamber 68 of the bioreactor can include an inlet chamber 70 that merges into hemi-chamber geometry describe above, and further into an out chamber 72. Scaffold 30 can be placed in the square recess 71 defined by chamber 68, as shown in FIG. 6C. The recess can be squared (7×7 mm$^2$) for receiving scaffold 30 (discussed infra, not show in in FIGS. 6C-6D), which featured four pillars that fixed the scaffold 30 in place, avoiding its potential movement under flow. The width of the inlet channel 70 of each bioreactor can be slightly smaller than that of the outlet channel 72 (0.65 mm and 1.3 mm, respectively), to reduce the chance of bubbles formation and retention during the perfusion. The inlet channel 70 and outlet channel 72 of each bioreactor were connected to TEFLON® micro tubes 69 (#30 AWG thin-wall tubing, made by Cole-Palmer), joined with a segment of silicone tubing to ensure sufficient oxygenation of the medium during culture. The silicone tubing was then fitted onto a peristaltic pump (for example, a MP2-4-PC Micro Peristaltic Pump, by Elemental Scientific) to allow perfusion. A 5-mL reservoir can be connected between the silicone tube and the inlet of the bioreactor to provide nutrients as well as to entrap bubbles. Epoxy was used to seal any possible source of leakage.

A photograph of an assembled bioreactor 60 can be seen in FIG. 6B. The structure and cooperation of structure of bioreactor 60 can be described more fully in a paper by Yu Shrike Zhang, et al., entitled "Multisensor-Integrated Organs-on-Chips Platform For Automated and Continual in situ Monitoring of Organoid Behaviors". The Zhang et al. paper also describes methods for monitoring the bioreactor 60, as well as alternative embodiments, and the Zhang paper is hereby incorporated by reference herein.

2.6. Computational Simulations

Initially, flow rates and oxygen distribution with the chamber can be simulated by computers (i.e. using a processor with written instructions input therein), as known in the prior art. One way to do this can be to use COMSOL MULTIPHYSICS® (Version 4.3b) to simulate the flow rates and oxygen distribution within the chamber of the bioreactor. Since the bioreactor was sandwiched by two pieces of gas-impermeable PMMA supports 62, the upper and lower boundaries can be considered oxygen-impermeable (zero mass flux) while lateral boundaries can be considered permeable due to the exposure of PDMS. The tissue constructs based on bioprinted fibrous scaffolds can be modeled as a hydrogel with uniform volumetric oxygen consumption rate associated with the total number of cells. Oxygen consumption rates at around $1.18 \times 10^{-4}$ mol/sec-cell for HUVECs and $1.14 \times 10^{-5}$ mol/sec-cell for cardiomyocytes, respectively, were assumed.

The numbers of the HUVECs and the cardiomyocytes can be estimated to be $7.70 \times 10^4$ (considering a total volume of the microfibrous scaffold of approximately 7.7 μL at a cell density of $1 \times 10^7$ cells mL$^{-1}$) and $4.00 \times 10^5$ per scaffold, respectively, according to the bioprinting/seeding conditions. The oxygen concentration at the inlet carried by the infusing medium was considered constant, uniform, and equal to the atmospheric concentration. The diffusion coefficient of oxygen in the culture medium and the hydrogel were approximated at $3.80 \times 10^{-9}$ m$^2$/sec and $2.30 \times 10^{-9}$ m$^2$/sec, respectively. A Michaelis-Menten kinetics was considered, assuming Michaelis constants of $0.55 \times 10^{-3}$ mol/m$^3$ and $6.88 \times 10^{-3}$ mol/m$^3$ for HUVECs and cardiomyocytes, respectively. A flow rate of 50 μL min$^{-1}$ was adopted after scaling down the flow rate of the blood in the heart according to the weights of the cardiac tissues. A symmetry condition along the long axis of the bioreactor chamber was considered and a numerical grid consisting of about $3 \times 10^7$ tetrahedral elements was applied.

2.7. Immunofluorescence Staining

Samples were fixed for 1 hour at room temperature using 4% volume paraformaldehyde (SIGMA-ALDRICH®) in PBS. Cells were permeabilized by soaking the samples in 0.1 vol. % Triton X-100 (by SIGMA-ALDRICH®) dissolved in PBS for 30 min while non-specific binding was inhibited using 10 vol. % bovine serum albumin (BSA, SIGMA-ALDRICH®) for 1 hour at room temperature. Samples were then incubated for overnight at 4° C. in a solution containing primary antibodies at 1:200 dilutions in 10 vol. % BSA and 0.1 vol. % Triton X-100 in PBS. In particular, rabbit polyclonal anti-CD31 (ab32457, ABCAM®), mouse monoclonal anti-sarcomeric α-actinin (ab9465, ABCAM®), and rabbit polyclonal anti-connecxin-43 (ab11370, ABCAM®) antibodies were used. Secondary antibodies were used at 1:200 dilutions. For F-actin staining, samples were incubated for 30 min at room temperature in a solution of Alexa 488-phalloidin (A12379, THERMO FISHER®) at 1:40 dilution in 10 vol. % BSA and 0.1 vol. % Triton X-100 in PBS. Nuclei of the cells were stained by 4', 6-diamidino-2-phenylindole (DAPI, THERMO FISHER®). Images were taken using a fluorescence optical microscope (Axio Observer D1 manufactured by ZEISS®) or a confocal fluorescence microscope (SP5×MP, provided by LEICA®).

2.8. Characterization of Tissue Constructs

Live/Dead staining was performed according to the manufacturer's instructions (THERMO FISHER®). Beating of the cardiomyocytes was observed using an optical microscope and analyzed using custom-coded MATLAB programs, as known in the prior art. Monitoring of the beating behavior was performed every day until contractions were no longer observed. It should be noted that due to the 3D nature of the constructs and the vibration of the media during the video recording, the beating plots obtained are expected to only accurately reflect the frequencies of the beating but no other functions. The levels of secreted vWF were measured by an ELISA kit (ab189571) by ABCAM®.

2.9. Statistics

When two groups were compared, statistical analyses were conducted using unpaired t-tests. When more than two groups were compared, analysis of variants (ANOVA) followed by a post-hoc test was performed. Statistical significance was determined at $p<0.05$. A sample size of at least 3-5 scaffolds per group was used.

3. Results and Discussions

3.1. Bioprinting 3D Microfibrous Scaffolds

Referring again to FIGS. 2A-2C, the 3D bioprinting approach of the systems and method of the present invention, can conveniently generate multilayer hydrogel microfibrous scaffolds using an Organovo Novogen MMX bioprinter 18 by NOVOGEN®, which was optimized through the implementation of a custom-designed coaxial nozzle extruder 20 for continuous extrusion of the bioink 26. The internal needle 22, having a size of 210 µm (27G), can be fed with a bioink 26 composed of a mixture of hydrogel precursors, i.e. alginate, GelMA, and photo initiator IRGACURE® 2959; the crosslinking solution, i.e. $CaCl_2$, can be simultaneously dispensed through an outer annular sheath defined by inner needle 22 and outer needle 24, using an outer needle 24 with size of 840 µm (18G, please see FIG. 2A). This specially designed bioink 26 was developed by modifying our recently developed protocol, as described more fully in a paper by Colosi C, et al., entitled "Microfluidic Bioprinting of Heterogeneous 3D Tissue Constructs Using Low Viscosity Bioink", Adv Mater. 2015;28:677-84. The contents of the Colosi paper are hereby incorporated herein by reference. The bioink 26 can feature a sequential crosslinking mechanism that can allow for stable production of 3D microfibrous scaffolds.

Figure 2B:
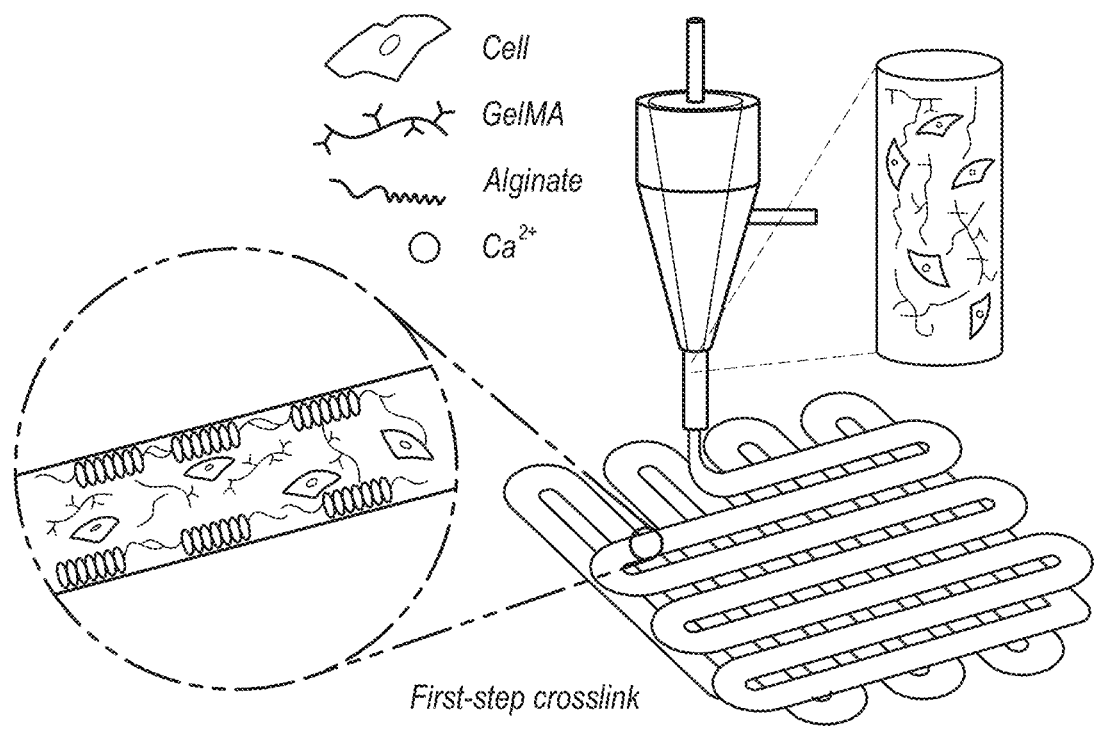

As indicated in FIG. 2B, when the two fluids come into contact at the tip of the printhead, a temporary ionic gelation of the alginate component in the bioink 26 can occur. This rapid gelation can lead to the formation of the microfibers and their deposition in the 3D space as programmed. More importantly, the constant wetting of the deposited microfibers by the co-extruded $CaCl_2$ solution further induces physical crosslinking of the microfibers between adjacent layers to stabilize the structure.

Figure 2C:
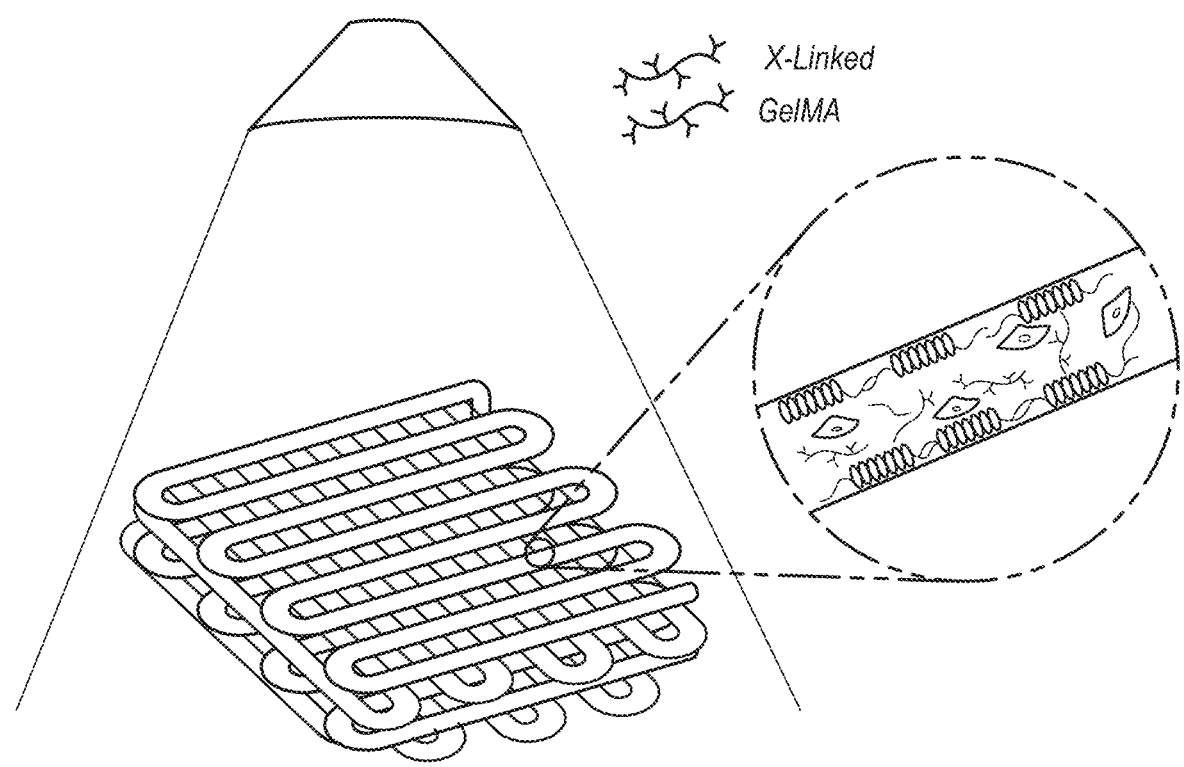
Figure 2D:
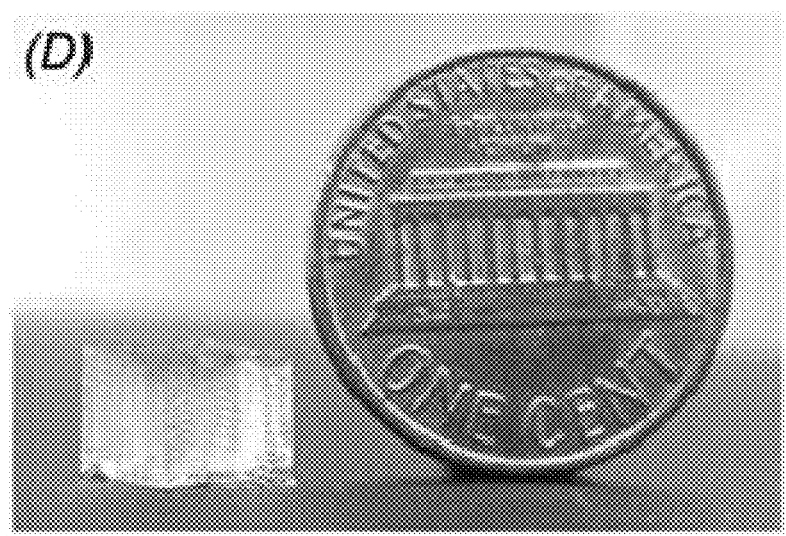

In addition, the $CaCl_2$ solution continuously provided through the external needle 24 can efficiently avoid scaffold dehydration during the bioprinting process. Subsequently, permanent chemical gelation of the microfibers can be achieved by exposing the scaffold to light to photocrosslink the GelMA component of the bioink. It is noteworthy to highlight that the temporary ionic crosslinking of the alginate is critical to ensure structural integrity of the bioprinted scaffolds, thus allowing for the generation of self-sustaining multilayered structures in a highly reproducible manner prior to chemical crosslinking, as shown in FIG. 2C. The alginate component of the bioink, 26 may eventually be washed off from the printed scaffolds following GelMA crosslinking using a solution containing $Ca^{2+}$-chelating agent such as ethylenediaminetetraacetic acid (EDTA), to promote cell adhesion and spreading.

Figure 2E:
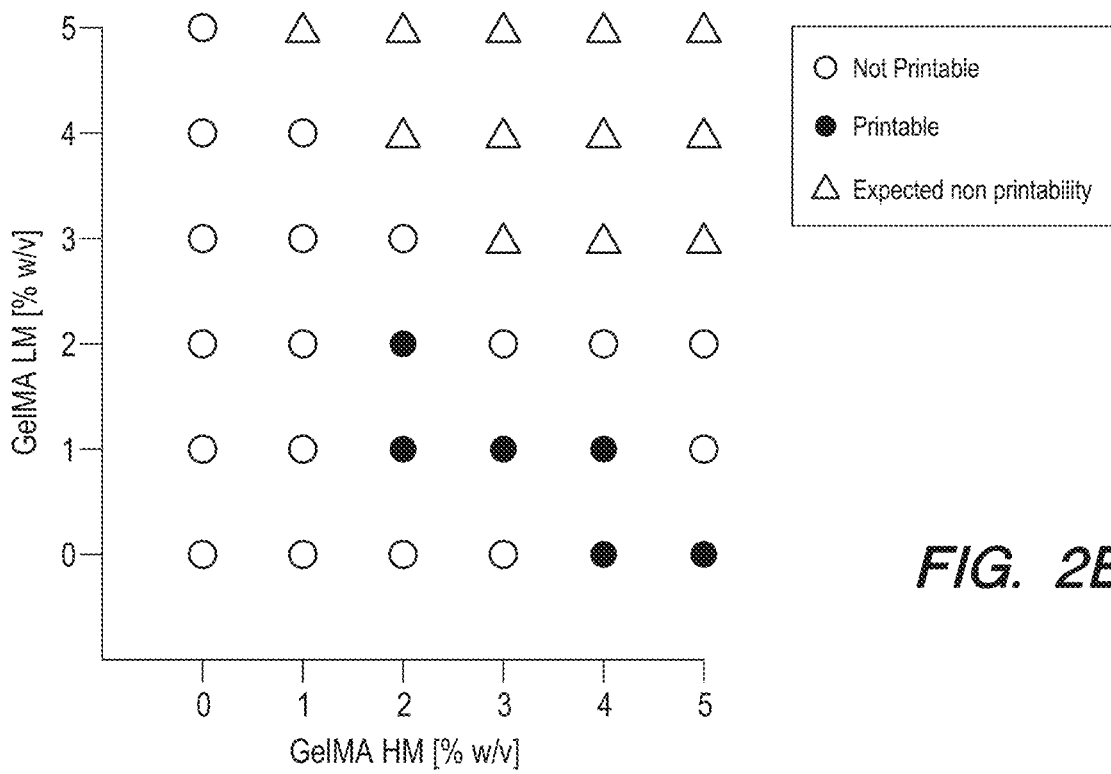

The bioink composition can be optimized to obtain a viscosity level compatible with a constant extrusion flow, in order to avoid clogging of the bioink 26 inside the nozzle extruder 20 while at the same time maintaining structural integrity of the resulting bioprinted microfibrous tissue constructs. Multiple candidate bioink 26 compositions were assessed for their printability. In particular, the concentrations of the alginate and photo initiator were maintained constant at 4 w/v % and 0.2 w/v %, respectively, while the relative concentrations of GelMA-HM and GelMA-LM were both varied in the range of 0-5 w/v %. FIG. 2E is a depiction of the assessment results. As can be inferred from FIG. 2E, the optimal composition of the bioink 26 can be found to include 3.5 w/v % GelMA-HM and 1 w/v % GelMA-LM, in addition to 4 w/v % alginate and 0.2 w/v % IRGACURE® 2959, and was used throughout the following experiments. A flow rate of 5 µL/min can be adopted for both the bioink 26 and the sheath crosslinking solution, while the extruder speed was set at 4 mm/s. The diameter of the resulting microfibers after complete swelling reached approximately 150 µm in diameter, in comparison to a size of 120 µm immediately after bioprinting.

Figure 3A:
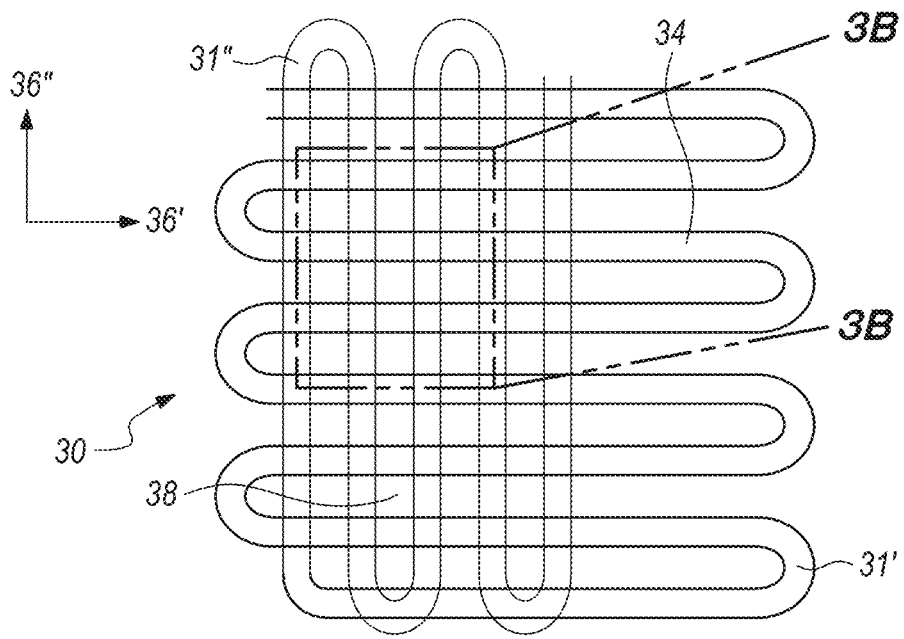
FIG. 3A can be a top plan view of a single-layer schematic of the design of the microfibrous scaffold of the present invention.
Figures 3B, 3C, 3D, 3E:
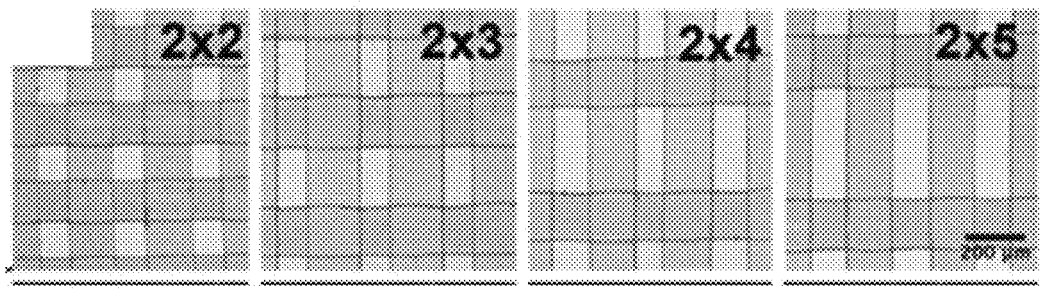
FIGS. 3B can be a brightfield micrograph of the portion 3B-3B shown in FIG. 3A
FIGS. 3C can be the same micrograph of FIG. 3B, but with a 2×3 aspect ratio of unit grids.
FIGS. 3D can be the same micrograph of FIG. 3B, but with a 2×4aspect ratio of unit grids.
FIGS. 3E can be the same micrograph of FIG. 3B, but with a 2×5 aspect ratio of unit grids.
Figures 3F, 3G, 3H, 3I:
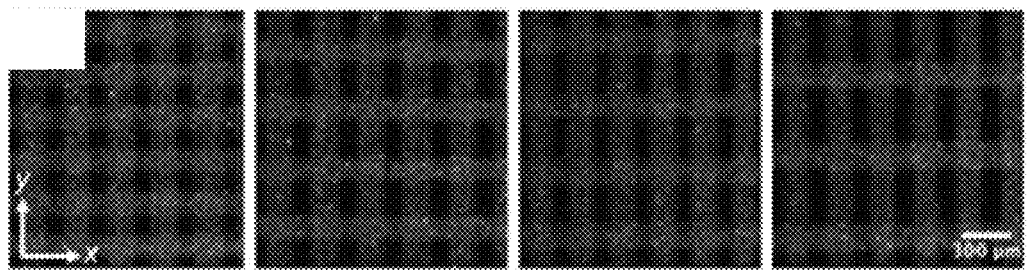
FIG. 3F can be a fluorescence micrograph of the brightfield micrograph of FIG. 3B.
FIG. 3G can be a fluorescence micrograph of the brightfield micrograph of FIG. 3C, FIG. 3H can be a fluorescence micrograph of the brightfield micrograph of FIG. 3D.
FIG. 3I can be a fluorescence micrograph of the brightfield micrograph of FIG. 3E.

It is known in the prior art that most biological tissues in the body are anisotropic, particularly in the case of the myocardium, where cardiomyocytes are uni-directionally aligned at cellular levels throughout the thickness of the tissue. Therefore, the systems and methods according to several embodiments can focus on the capability of the systems and methods to bioprint 3D microfibrous scaffolds with anisotropic arrangements. Referring now to FIGS. 3A and 3B, an exemplary rectangular scaffold 30 with an aspect ratio of the unit grid of 2×2 can be used as the isotropic control. As shown in FIGS. 3A and 3B, scaffold 30 can include a plurality of serpentine layers 31, with each layer having a plurality of tines 34 arranged along a primary axis 36. As shown in FIGS. 3B-3E, the serpentine layers 31 can be arranged so that successive layers 31 (for example, layers 31' and 31" in FIG. 3B) can be arranged so that the primary axis 36', 36" of successive layers is substantially perpendicular. With this configuration above a plurality of rectangular holes 38 can be established in the scaffold when it is viewed in top plan, and the rectangular holes 38 can have an aspect ratio, or a ratio of height and width dimensions for the hole 38. As also shown in FIGS. 3B-3E, one aspect ratio could be 2×2. But the 2×2 aspect ratio could be enlarged, from a 2×2 aspect ratio, to 2×3, 2×4, and 2×5 aspect ratios, respectively, to produce scaffolds with gradually increasing overall anisotropy at macroscale (FIGS. 3B-3E). Other aspect ratios are certainly possible, according to needs of the end user of the scaffold 30.

To establish the aspect ratio described above, the anisotropic scaffolds 30 can be fabricated by varying the distance between the fibers deposited in the y direction (perpendicular with the primary axis 36) while keeping the distance constant in the direction (parallel to the primary axis 36) at 220 μm. The distance between the central axes of the adjacent microfibers deposited in the y direction was increased stepwise from 220 μm, i.e. the isotropic control with 2×2 aspect ratio of the unit grid (FIG. 3B), to 330 μm, 440 μm, and 550 μm, for anisotropic scaffolds with unit grids containing aspect ratios of 2×3, 2×4, and 2×5, respectively (FIGS. 3C-3E). As shown in FIGS. 3F-3I, optical microfibers were pseudo colored in two different hues to mark the microfibers in the two perpendicular directions and fluorescence. In FIGS. 3F-3I, green fluorescent microbeads were added to the bioink prior to printing. The micrographs of the bioprinted scaffolds can confirm that the distance between the microfibers was in agreement with our predictions. The resulting spacing between the microfibers in the x direction was 226.3±5.3 μm, whereas the spacing between those in the y direction became 229.3±8.8 μm, 326.0±7.7 μm, 451.0±12.5 μm, and 563.0 ±9.1 μm in the four types of scaffolds with increasing anisotropy, respectively.

Figure 3J:
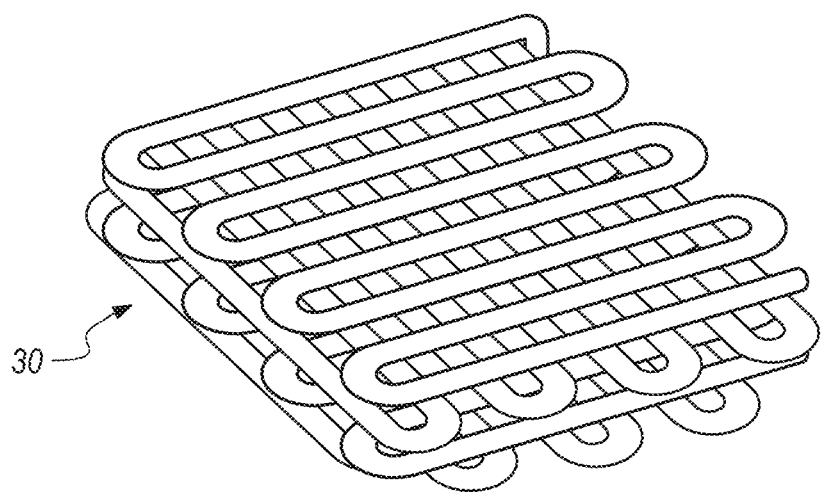
FIG. 3J can be an elevational view of a multi-layer microfibrous scaffold of FIG. 3A, without offset.

It was found, however, that for some aspect ratios in the bioprinted multi-layer scaffold, the junction sites where the interlacing microfibers laid over each other slightly collapsed due to the compression incurred by the weight of the partially cross-linked bioink. As example of this phenomena can be seen in FIGS. 3J-3L. Such compression can inevitably reduce the space between the microfibers (see FIG. 3L), which might limit the seeding efficiency of the cardiomyocytes at a later stage. In order to maximize the surface area of the microfibrous scaffolds exposed to cardiomyocytes during the seeding process for their attachment, an offset distance 32 between the alternating scaffold layers 31', 31" that have the same primary axis 36 (See FIG. 3M) of the microfibers was further incorporated into the design of the bioprinting process. In this case, the overall layer of microfibers along the long axis of the unit grids was shifted by an offset distance 32 of one half unit grid, can result in significantly increased surface-to-volume ratio of the microfibers without influencing the overall porosity of the scaffolds (FIGS. 3M-O; 2×5). The microfibers in both the schematics and optical micrographs were labeled in red and blue in alternating layers to clearly demarcate the shift. The microfibers along the short axis of the unit grids were designed to remain in the same positions to support the three-dimensionality of the bioprinted scaffolds (FIGS. 3M-O).

Figure 3P:
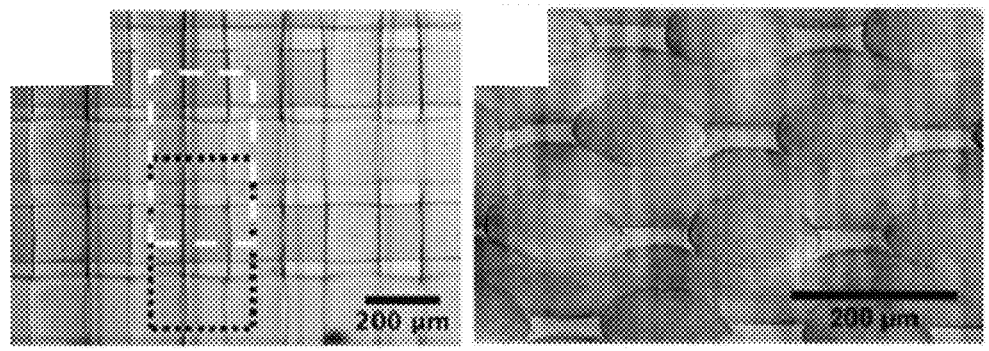
FIG. 3P can be a histogram of elastic modulus of the bioprinted scaffolds for the different aspect ratios of shown in FIGS. 3B-3I.
Figure 3P:
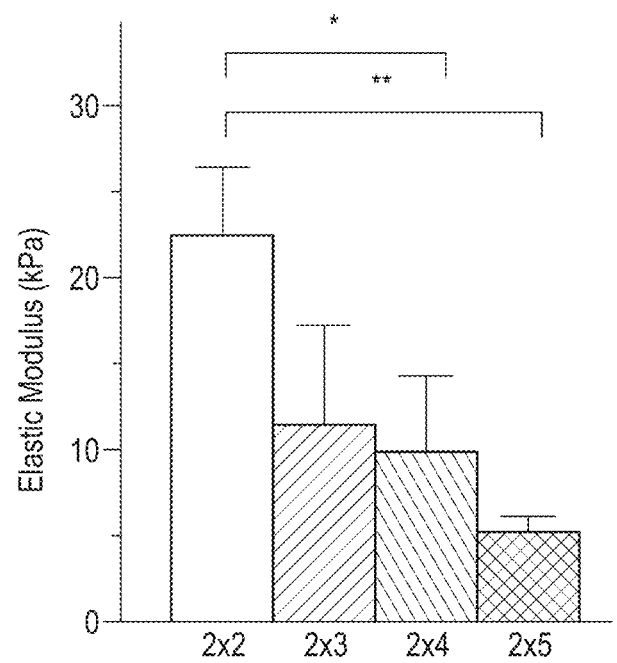

Mechanical properties of scaffolds with different aspect ratios of the unit grid were further characterized in the histogram depicted in FIG. 3P). The results indicated that the elastic modulus of the bioprinted scaffolds can be dependent on the distance between the adjacent microfibers caused by the difference in the aspect ratio of the unit grid, which is linked to the porosity of the scaffold. Theoretical porosities of the four types of bioprinted scaffolds were calculated to be 37.2%, 43.2%, 46.9%, and 49.4% for those with aspect ratios of unit grids of 2×2, 2×3, 2×4, and 2×5, respectively. As seen in FIG. 3P, the measured elastic modulus of the 2×2 scaffolds (22.6±3.9 kPa) can be higher than those of both scaffolds with aspect ratios of 2×4 (9.9±4.4 kPa; $p<0.05$) and 2×5 (5.2±0.9 kPa; $p<0.01$) for the unit grids, whereas the modulus of the 2×3 scaffolds was 11.5±5.8 kPa). These results can be in good agreement with previously reported data, which showed compressive moduli on the order of 20-30 kPa for isotropic microfibrous scaffolds of similar structure and material.

3.2. Construction of Endothelialized Myocardium

Vascularization presents one of the most critical steps during the development of many functional tissue and organ systems since mature networks of blood vessels enable the transport of nutrient, oxygen, and wastes to/from the tissues. This is particularly true for highly metabolically active organs including the heart. A plethora of strategies have been developed in the prior art to promote the vascularization of tissue constructs. Conventional approaches of vasculogenesis and angiogenesis relying on self-organization of endothelial cells into interconnected capillary structures are limited by their variability and efficiency. Recently, bioprinting has emerged as a highly reproducible and versatile strategy to deposit sacrificial microfibers within hydrogel matrices; following template dissolution or removal, the hollow microchannel network could then be endothelialized to generate perfusable microvessels. The systems and methods of the present invention according to several embodiments can further propose a hybrid technology combining guided self-assembly and 3D bioprinting to develop endothelialized tissue constructs by encapsulating endothelial cells within the GelMA-alginate bioink to fabricate scaffolds possessing a biomimetic anisotropic pattern. These multilayer scaffolds could be subsequently cellularized by cardiomyocytes to generate the endothelialized myocardial constructs.

3.2.1. Endothelialization of the Bioprinted Microfibrous Scaffolds

Figure 4A:
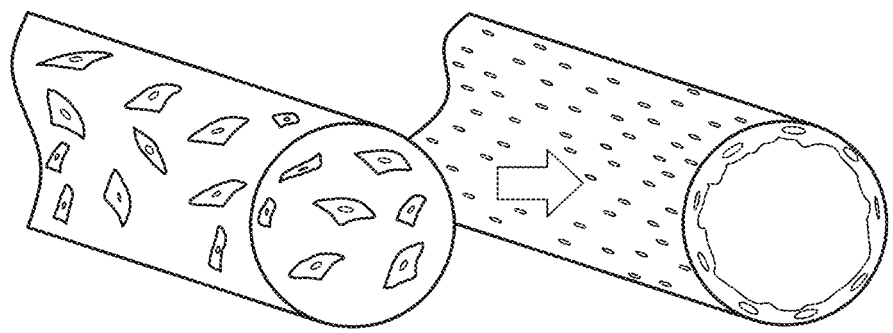
FIG. 4A can be a schematic representation which can show the assembly of the encapsulated human umbilical vein endothelial cells (HUVECs) inside the bioprinted microfibers into a confluent layer of endothelium.
Figure 4B:
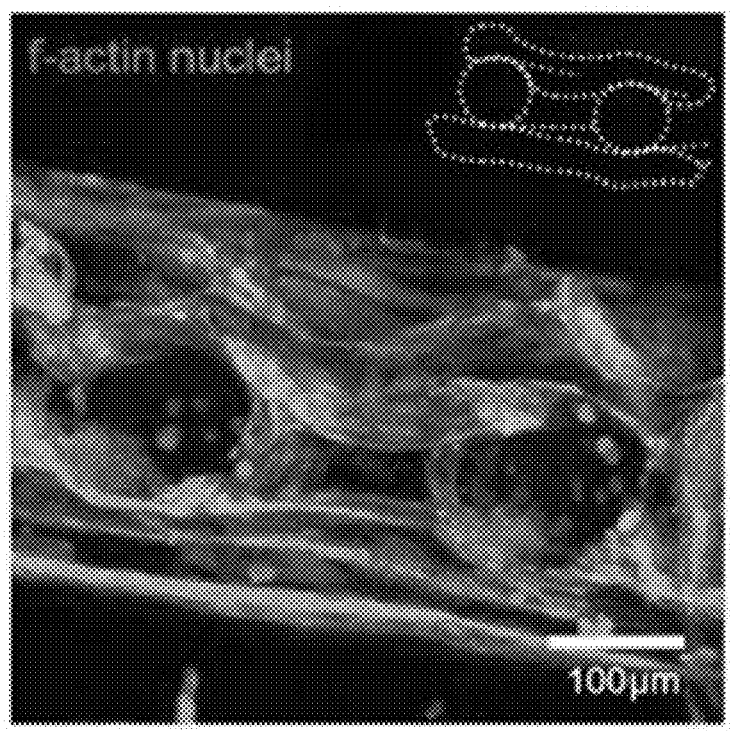
FIG. 4B can be a cross-sectional confocal fluorescence micrograph showing the cross-sectional view of a three-layer scaffold at Day 14, which can indicate the formation of the endothelium by the HUVECs.
Figure 4C:
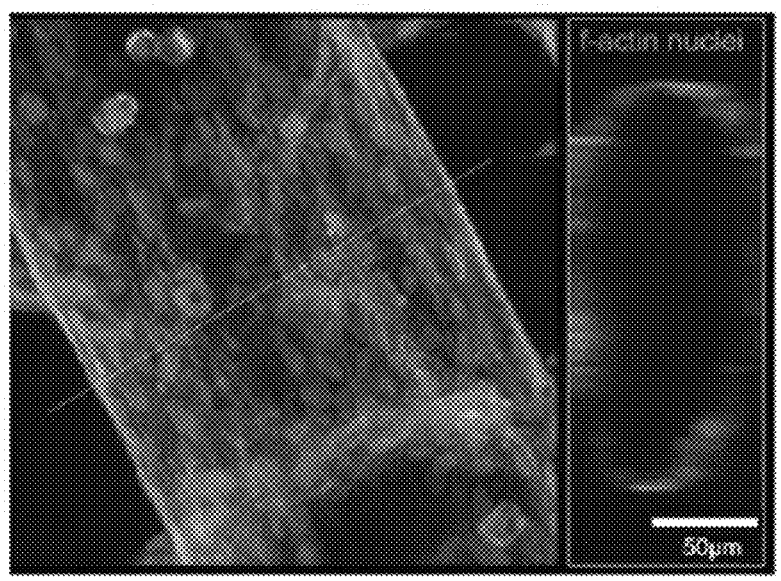
FIG. 4C can be a higher-resolution confocal fluorescence micrograph of the micrograph of FIG. 4B.
Figure 4D:
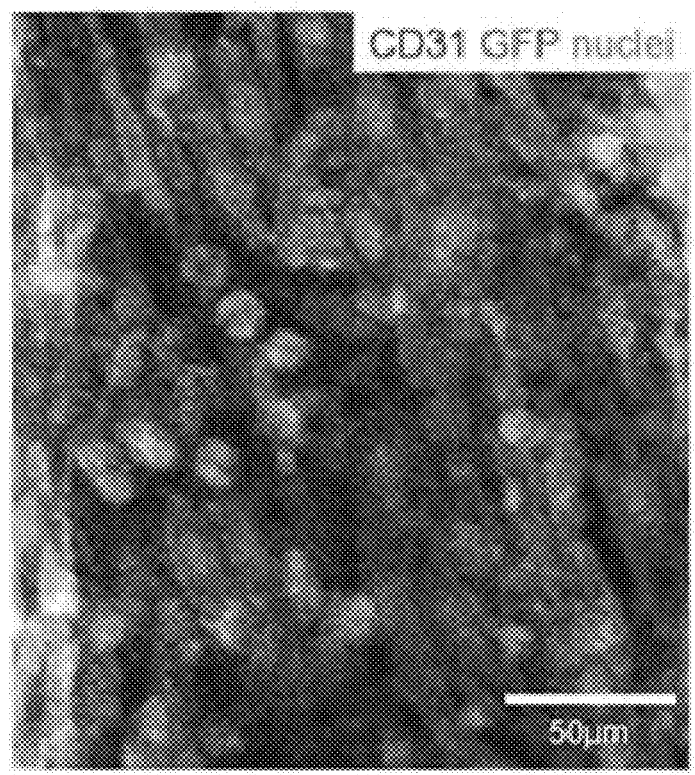
FIG. 4D can be a confocal fluorescence micrograph showing the GFP-HUVECs in a single fiber for cluster of differentiation 31 (CD31), green fluorescent protein (GFP), and nuclei.
Figures 4E, 4F, 4G, 4H:
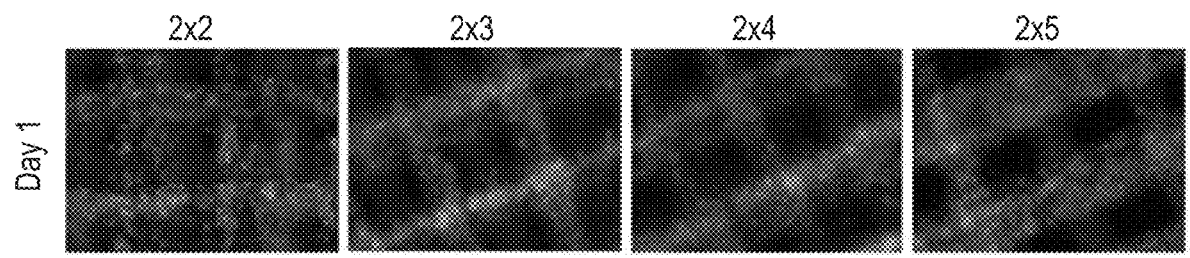
FIG. 4E can be a fluorescence micrograph showing the distribution and spreading of GFP-HUVECs in a bioprinted microfibrous scaffolds with a 2×2-unit grid aspect ratio at day 1.
FIG. 4F can be the same fluorescence micrograph as FIG. 4E, but for a 2×3-unit grid aspect.
FIG. 4G can be the same fluorescence micrograph as FIG. 4E, but for a 2×4-unit grid aspect.
FIG. 4H can be the same fluorescence micrograph as FIG. 4E, but for a 2×5-unit grid aspect.
Figures 4I, 4J, 4K, 4L:
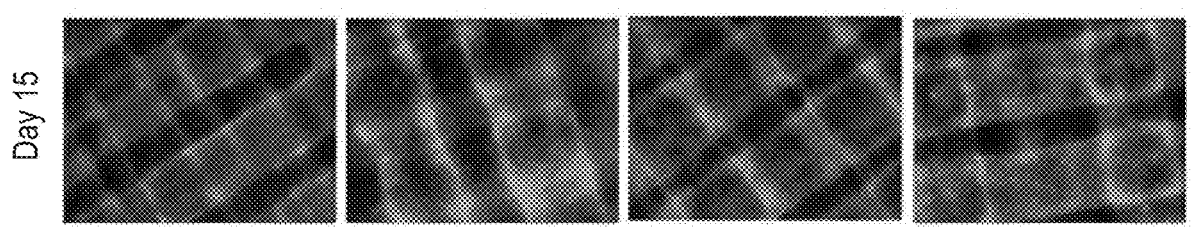
FIG. 4I can be the same micrograph as FIG. 4E, but at day 15.
FIG. 4J can be the same micrograph as FIG. 4F, but at day 15.
FIG. 4K can be the same micrograph as FIG. 4G, but at day 15.
FIG. 4L can be the same micrograph as FIG. 4H, but at day 15.

The bioink and methods for employment in accordance with the systems and methods of the present invention, can possess strong biocompatibility, which can further readily allow for the embedment of cells during the bioprinting process. Interestingly, it was found that following the bioprinting of the scaffolds, the HUVECs, initially homogeneously dispersed within the microfibers, could gradually organize into a layer of confluent endothelium surrounding the microfibers after approximately 2 weeks of culture, potentially through migration towards the peripheries (FIG. 4A). FIG. 4B can be a confocal image of the cross-section of a three-layer scaffold at Day 15 clearly revealed that the HUVECs concentrated at the borders of the microfibers, forming a pattern resembling the blood vessel walls. FIG. 4C can show the magnified high-resolution confocal projection and reconstruction images of a single microfiber shown, and can further confirm the confluency of the HUVECs at the entire periphery of the microfiber at Day 15 of culture, resulting in a lumen-like structure with 83.1±5.4% area occupation. In addition, the endothelial cells expressed surface marker CD31, forming tight junctions among adjacent cells in the confluent layer, as can be seen from the portions in red in FIG. 4D.

The chronological evolution of the formation of the endothelium by GFP-HUVECs inside the bioprinted microfibrous scaffolds 30 is shown in FIGS. 4E-4H (for 2×2, 2×3, 2×4 and 2×5 aspect ratios, respectively, at day 1) an also for FIGS. 4I-4L (for 2×2, 2×3, 2×4 and 2×5 aspect ratios, respectively, at day 15). The HUVECs were homogeneously distributed inside the microfibers at Day 1 post bioprinting (FIGS. 4E-4H); the HUVECs gradually migrated towards the peripheries of the microfibers. The migration was potentially driven by the intrinsic polarization tendency of these cells to stay at the liquid-matrix interfaces as well as the higher availability of nutrients and oxygen surrounding the microfibers. It can be further discovered that the ionically cross-linked alginate component could dissolve in the culture medium and leach out from the bioprinted microfibers in approximately 5-10 days.

Since the microfibers were better ionically cross-linked for the alginate component at the peripheries during the bioprinting process, the release of alginate can result in the formation of larger pores along the borders, which can further promote the spreading and proliferation of the HUVECs, eventually forming well-patterned endothelium in approximately 15 days of culture (FIGS. 4I-4L). It was found that the density of the initially encapsulated HUVECs did not play a significant role in such a migration process, with migration observed across a wide density range of $1-15 \times 10^6$ cells/mL. However, the density did impact the formation of the lumen-like structure as overly small cell densities could not result in the formation of intact endothelium while excessive cells led to aggregation within the microfibers. Therefore, an optimized encapsulation density of the HUVECs of $10 \times 10^6$ cells/mL can be used for some embodiments.

At the shared borders between the overlapping microfibers, the HUVECs appeared to re-organize, defining an interconnected region between those of different layers (FIGS. 4I-4L). Importantly, the aspect ratios of the unit grid of the bioprinted microfibrous scaffolds did not remarkably alter their capability to endothelialize. However, it was found that the morphologies of the HUVECs did not significantly change during the rest of the culture for up to 33 days observed; in contrast, they gradually broke the boundaries of the microfibers and migrated out to the bottom of the microwells, likely due to the degradation of the GelMA and thus impaired integrity of the microfibrous structures. As a consequence, the bioprinted microfibrous scaffolds 30 embedded with HUVECs were maintained in culture for 15 days throughout the subsequent experiments. These findings can suggested that bioprinting techniques of the present invention, using a bioink specially designed to possess a dual-step crosslinking mechanism, can provide for the formation of 3D endothelialized networks of any desired shape and architecture.

The crossing microfibers in the bioprinted scaffolds possessing macroscale anisotropy should not affect final functionality of the endothelialized myocardium, since the microvascular network within the native contractile myocardium is not strictly aligned with the direction of the cardiomyocytes. It should be further noted that, although the endothelialized microfibers were not hollow during the period analyzed, our bioprinted microfibrous network could provide excellent guidance for endothelialization in the entire volume. We expect that, when these endothelialized scaffolds are further embedded within tissue constructs, the degradation of the hydrogel in the interior may eventually open up the channels and form hollow lumens that will enhance the functionality of the spatially defined vascular network. However, the proof of such hypothesis needs further experimental validation and will be reported in the future.

3.2.2. Construction of the Myocardium

Figure 5A:
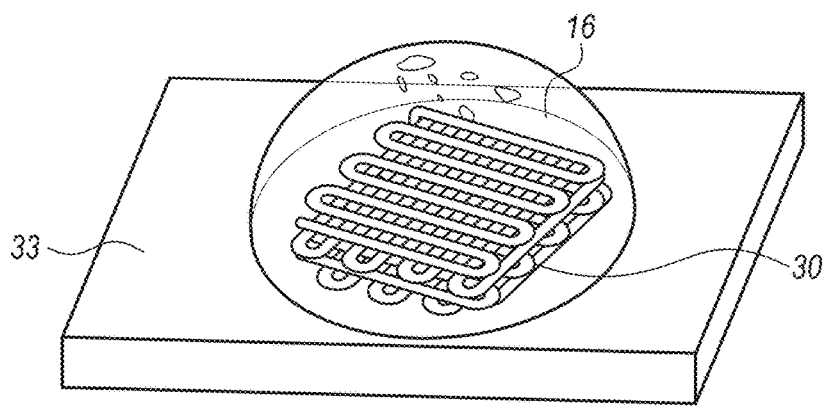
FIG. 5A can be a depiction that illustrates the seeding procedure of cardiomyocytes onto the bioprinted microfibrous scaffolds.
Figure 5B:
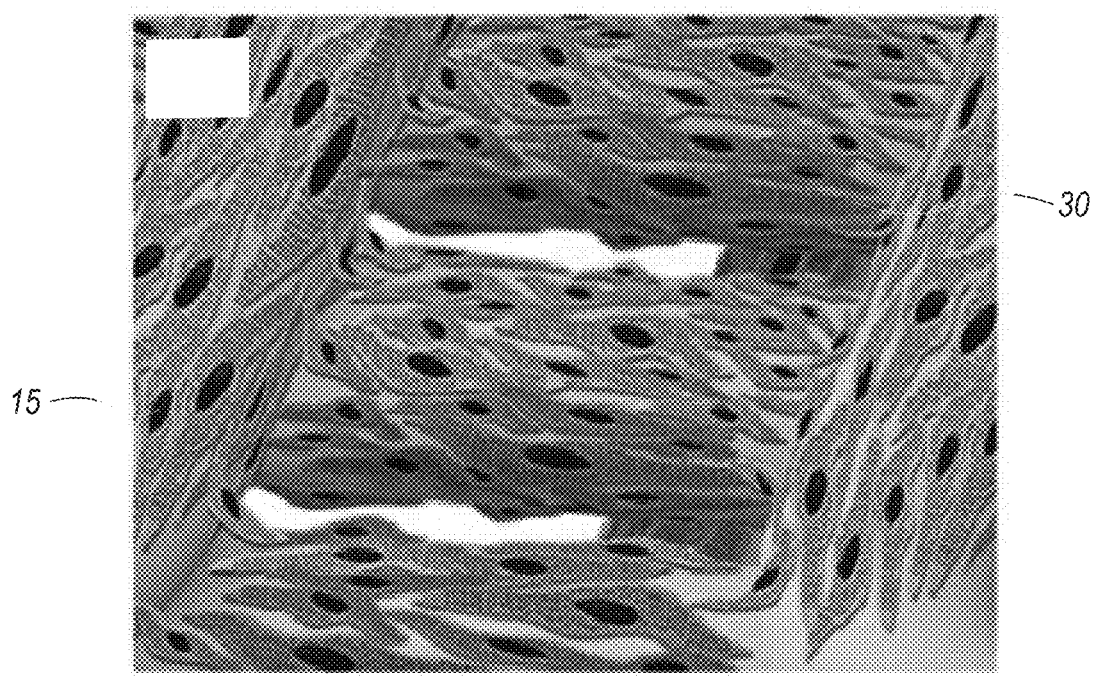
FIG. 5B can be a schematic of a scaffold of FIG. 5A that has been seeded with neonatal rat cardiomyocytes.

The possibility of employing the bioprinted microfibrous scaffolds as substrates for the construction of cardiac tissues using the systems and methods according to several embodiments can be explored. To do this, rat neonatal cardiomyocytes can be used as the model cells due to their abundant availability. The cells were seeded (suspension cloud 16 in FIG. 5A) into bioprinted microfibrous scaffolds lodged on top of hydrophobic polydimethylsiloxane (PDMS) surfaces 34, FIG. 5A. Such a hydrophobic platform can be adopted to ensure that cell suspensions for seeding could be directly laid over the scaffolds without spreading, thus leading to the attachment of a high density of the cardiomyocytes 15 on the microfibers of the scaffolds 30, as depicted in FIG. 5B.

Figure 5C:
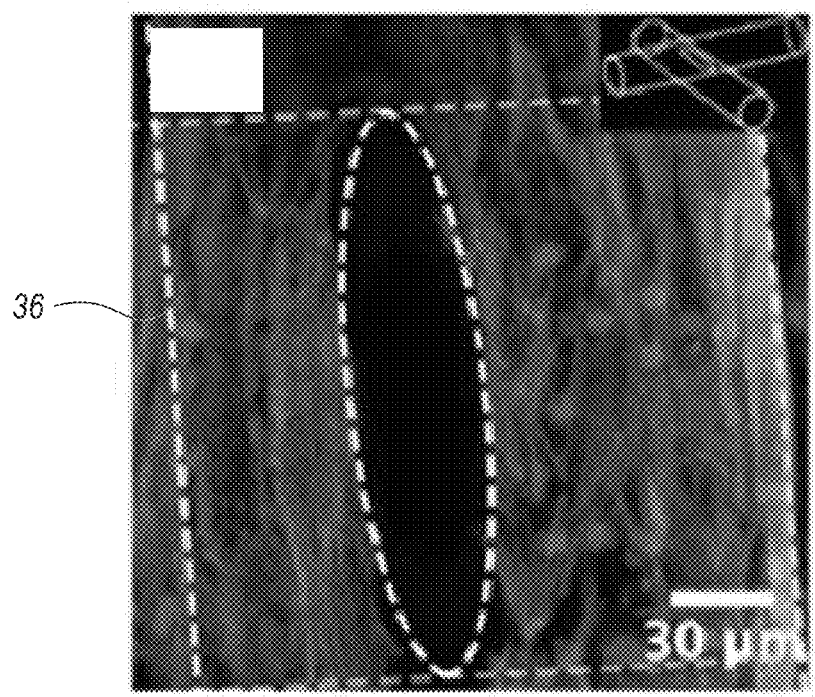
FIG. 5C can be a F-actin (green) staining showing the distribution of the cardiomyocytes on the surface of the scaffold of FIG. 5B at the location where two microfibers of adjacent layers crossed.
Figures 5D, 5E, 5F, 5G:
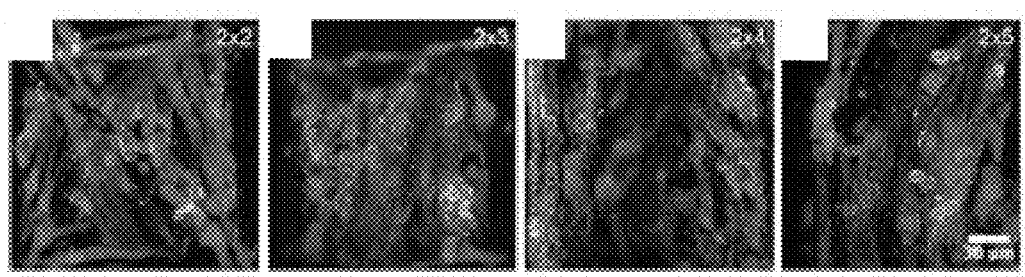
FIG. 5D can be a photograph of immunofluorescence staining of sarcomeric α-actinin (red) and connexin-43 (Cx-43, green) of cardiomyocytes seeded on bioprinted microfibrous scaffolds with a 2×2 aspect ratio.
FIG. 5E can be the photograph of FIG. 5D but for a scaffold with a 2×3 aspect ratio.
FIG. 5F can be the photograph of FIG. 5D but for a scaffold with a 2×4 aspect ratio.
FIG. 5G can be the photograph of FIG. 5D but for a scaffold with a 2×5 aspect ratio.
Figures 5H, 5I, 5J, 5K:
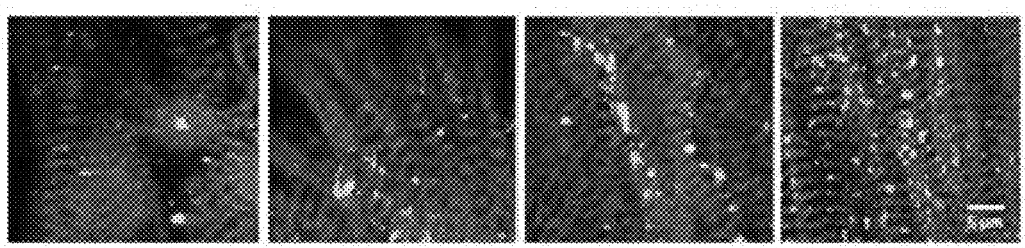
FIG. 5H can be a magnified image of 5D, which can show illustrate sarcomeric banding.
FIG. 5I can be a magnified image of 5E, which can show illustrate sarcomeric banding.
FIG. 5J can be a magnified image of 5F, which can show illustrate sarcomeric banding.
FIG. 5K can be a magnified image of 5G, which can show illustrate sarcomeric banding.

In particular, scaffolds 30 having a dimension of $3.5 \times 5.5$ mm$^2$ and 5 layers 31 of interlacing microfibers can be used to sufficiently recapitulate the three-dimensionality of the myocardium, while also minimizing the amount of cells required for the experiments. In order to simulate the conditions of endothelialized scaffolds, for the experiments where no HUVECs were encapsulated in the microfibers, the scaffolds were still incubated for 15 days in the medium prior to seeding for behavioral analysis of cardiomyocyte monoculture. Immediately post seeding, the density of the adhered cardiomyocytes was measured and no significant differences were observed among the scaffolds with different aspect ratios of the unit grid ($2 \times 2$:1883±415 cells/mm$^2$; $2 \times 3$:1896±651 cell/mm$^2$; $2 \times 4$:2020±147 cells/mm$^2$; $2 \times 5$: 1773±335 cells/mm$^2$). Myocardial constructs were then cultured for 3 days to allow for the maturation of the cardiomyocytes. The cardiomyocytes uniformly adhered onto the surface of the microfibers in the scaffolds, leaving space at the junction points formed between two crossing microfibers in adjacent layers, which can be illustrated by the white dotted line oval in FIG. 5C. The cardiomyocytes adhered and spread on the surface of the microfibers across the entire thickness of the scaffolds due to a combinatory effect of gravity, diffusion, and capillary force during the seeding process.

It can be noteworthy that cardiomyocytes grown on the bioprinted microfibrous scaffolds strongly expressed proteins that are necessary for proper contractile function, i.e. sarcomeric a-actinin, and inter-cellular conductive function, i.e. connexin-43 (Cx-43), as demonstrated by the immunostaining micrographs of FIGS. 5D-G, which correspond to scaffolds 30 have aspect ratios of $2 \times 2$, $2 \times 3$, $2 \times 4$ and $2 \times 5$, respectively. Indeed, the presence of organized sarcomeric banding and the formation of a large number of gap junctions provided evidence of the maturation of the cardiomyocytes and represented a critical basis for generating synchronous beating of the cardiac constructs. In addition, Cx-43 expression (in terms of percentages of area coverage) was higher for cardiomyocytes on samples with macroscale anisotropy ($2 \times 3$:3.59±0.32%; $2 \times 4$:5.49±0.48%; and $2 \times 5$: 8.02±0.54%; area coverage) when compared to the isotropic controls ($2 \times 2$:2.23±0.30%), as depicted by the histogram in FIG. 5L.

Figure 5L:
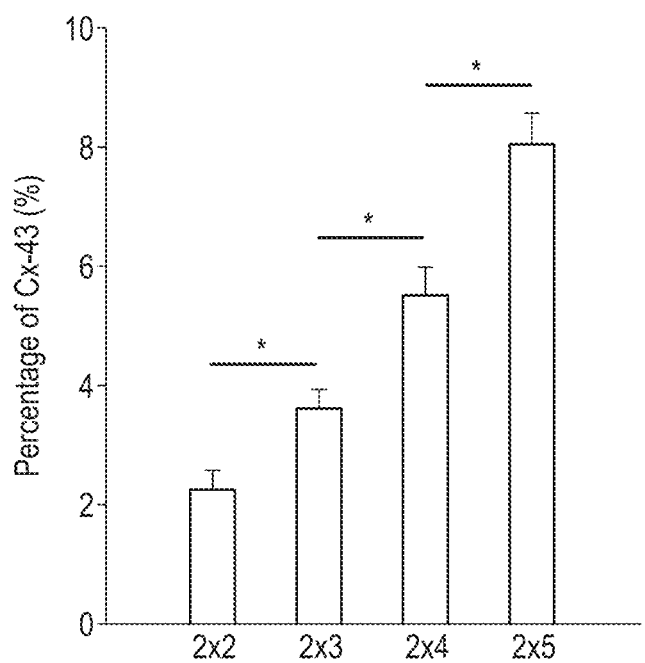
FIG. 5L can be a quantification of Cx-43 expression by the cardiomyocytes on the four types of scaffolds of FIGS. 5D-5G, plotted as percentages of area coverage calculated from fluorescence images, with *$p<0.005$.
Figure 5M:
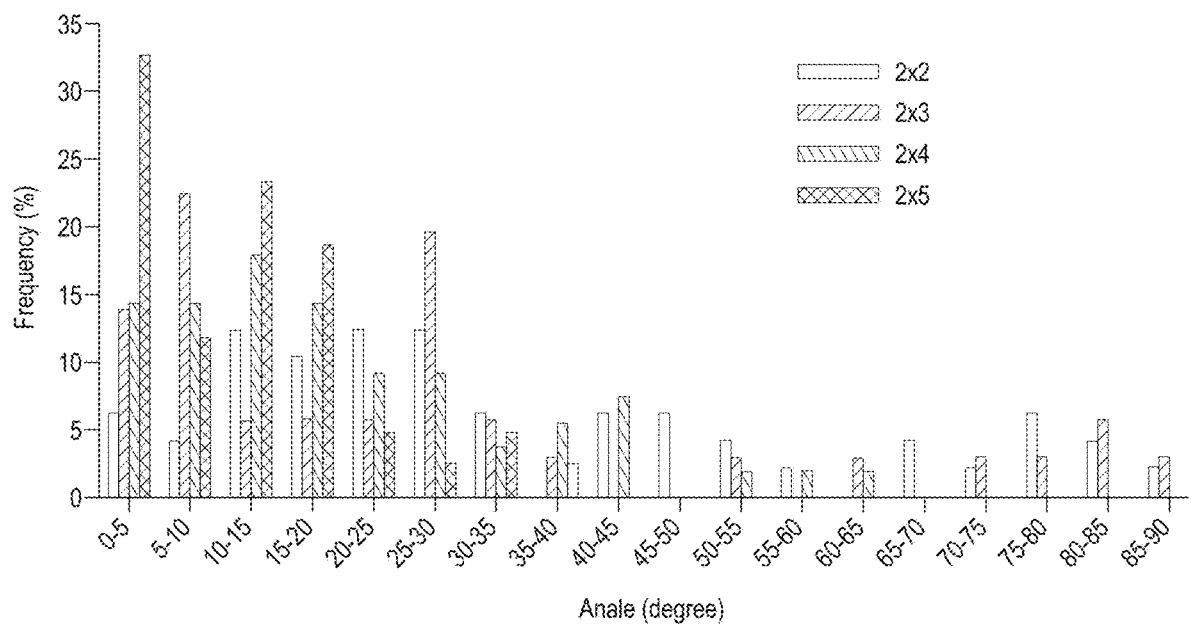
FIG. 5M can be a graph of Frequency percentage versus angle, which shows a quantification of the angle distribution of cardiomyocytes on the bioprinted microfibrous scaffolds of FIGS. 5D-5G.

The alignment of the cardiomyocytes on bioprinted scaffolds with different aspect ratios of unit grids was further analyzed by quantifying the angles between individual cells and the long axis of the grids. Referring to FIG. 5M, an angle equal to 0° referred to cells that were perfectly aligned in the direction of long axis of the unit grids, while an angle of 90° indicated perpendicularly alignment of the cells, i.e. along the short axis of the unit grids. It was revealed that the cardiomyocytes aligned increasingly better even at the cellular level in the direction of the microfibers along the long axis as the macroscopic anisotropy of the bioprinted scaffolds was increased (FIG. 5D-5L). As expected, the isotropic controls presented an almost uniform distribution of the orientation of the cardiomyocytes. On the contrary, scaffolds with the highest macroscale anisotropy ($2 \times 5$) were characterized by cardiomyocytes with alignment angles all lower than 40°, and most angles fell within the range of 20°. This observation is in agreement with previous studies, where anisotropic scaffolds induced much higher alignment of cardiomyocytes than anisotropic controls.

The spontaneous beating of the cardiac tissue constructs started after 48 hours of culture for scaffolds with aspect ratios of unit grids of 2×2 and 2×3, and after 72 hours for 2×4 and 2×5 samples. The cardiomyocyte-populated scaffolds 30 were beating synchronously and only slight transient shrinkage in the length of the microfibers during the contractions could be observed. The contraction amplitudes of the constructs can be compared as a function of the aspect ratios of unit grids of the scaffolds. In particular, the distances between the nuclei of adjacent cells during contraction (D) and relaxation ($D_0$) were measured. To compare the results across different samples, the difference between the two distances were further normalized against that during relaxation (i.e. ($D_0$-D)/$D_0$). The resulting value, denoted as the contraction amplitude, may partially reflect the contraction force generated by the cardiomyocytes, and is also associated with the intrinsic physical properties of the scaffolds. As shown in FIG. 5M, the contraction amplitude increased with the macroscale anisotropy of the scaffolds at both Day 3 (2×2 aspect ratio: 3.82±1.50%; 2×3 aspect ratio: 8.70±1.81%; 2×4 aspect ratio: 10.98±3.06%; and 2×5 aspect ratio: 12.62±4.79%) and Day 7 (2×2 aspect ratio: 5.90±3.00%; 2×3 aspect ratio: 8.08±2.77%; 2×4 aspect ratio: 11.39±2.89%; and 2×5aspect ratio: 12.39±1.81%).

Figure 5N:
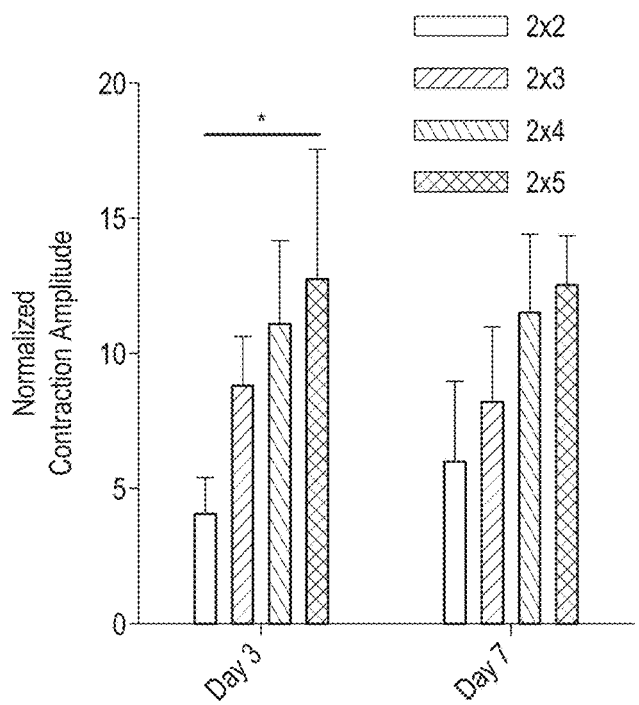
FIG. 5N can be a graph of the contraction amplitude of the four types of bioprinted myocardial constructs of FIGS. 5D-5G for *$p<0.05$, FIG. 5O can be a graph of contractions versus time, which can show a beating analysis of the cardiac organoid on the bioprinted scaffold of FIG. 5D.
Figure 5O:
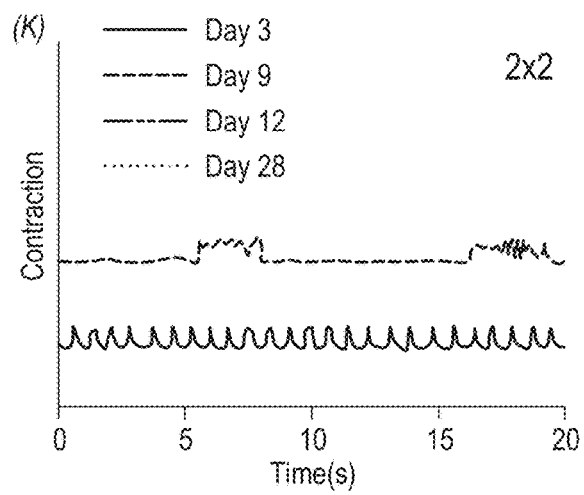
FIG. 5P a graph of contractions versus time, which can show a beating analysis of the cardiac organoid on the bioprinted scaffold of FIG. 5E.
FIG. 5Q can be a graph of contractions versus time, which can show a beating analysis of the cardiac organoid on the bioprinted scaffold of FIG. 5F.
FIG. 5R can be a graph of contractions versus time, which can show a beating analysis of the cardiac organoid on the bioprinted scaffold of FIG. 5G.
Figure 5P:
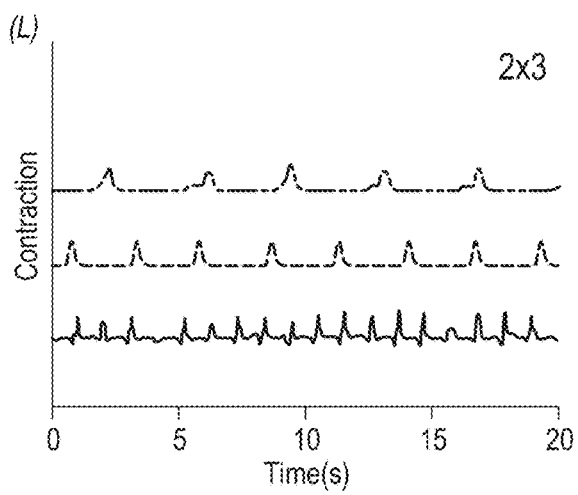
Figure 5Q:
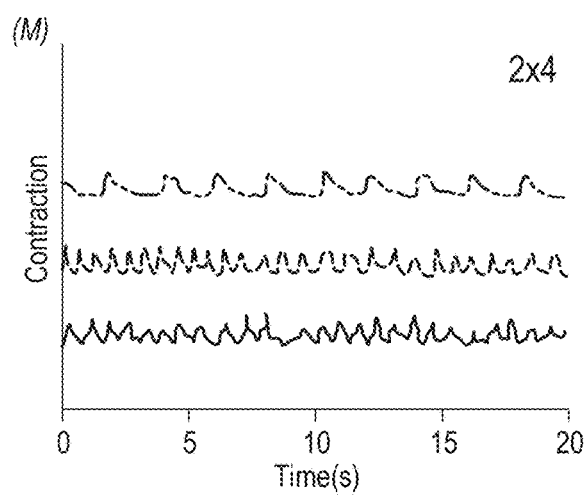
Figure 5R:
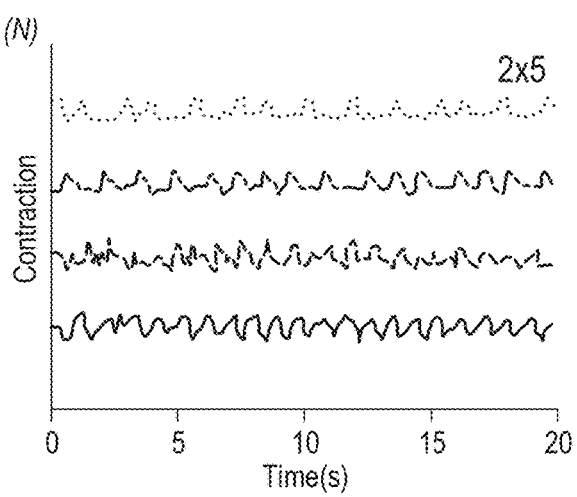

Beating frequencies over time for scaffolds 30 with different aspect ratios 2×2, 2×3, 2×4, 2×5 of unit grids, (and thus the alignment and maturation of the cardiomyocytes) were subsequently quantified. Representative contraction plots of the cardiac tissue constructs at Days 3, 9, 12, and 28 can be illustrated in FIG. 5O-R. In all four types of samples, the beating of the cardiomyocytes was robust during the first few days, ranging from 55-75 beat per min (bpm) depending on the scaffolds, while the contraction of each individual construct was uniform. However, the beating of the cardiomyocytes on isotropic scaffolds (2×2) significantly slowed down with possible arrhythmia after 9 days (FIG. 5O). On the contrary, cardiomyocytes seeded on 2×3 and 2×4 scaffolds continued beating until Days 15-22, although the frequencies slightly decreased over the period (FIG. 5L-N). The longest contraction was observed for 2×5 scaffolds (3 out of 4 samples) for up to 28 days, while the beating frequency was still maintained at approximately 40 bpm. This result was in good agreement with cardiomyocyte alignment, Cx-43 expression, and contraction amplitude analyses.

The improvement in the beating of the cardiac constructs with the increase in the macroscale anisotropy of the scaffold might be related with the alignment of the cardiomyocytes at the cellular level. Indeed, in 2×2 and 2×3 scaffolds the cardiomyocytes showed insufficient alignment at cellular level, possibly leading to an early but immature phenotype with limited beating capacity. In contrast, for scaffolds with 2×4 and 2×5 aspect ratios of unit grids, the cardiomyocytes were able to fully align even at the cellular level in the direction along the long axis, so that delayed but more complete maturation and prolonged beating could be achieved. In addition, the difference in the beating behaviors might be partially attributed to the slightly decreased elastic modulus of the scaffolds as the aspect ratio of the unit grids was increased (FIG. 3P). It is believed that, since the densities of the cardiomyocytes on each type of scaffolds did not differ significantly, the decreasing total amounts of cells on scaffolds with increased macroscale anisotropy should have not have affected the beating behaviors of the scaffolds.

Overall, it can be demonstrated that by tuning the macroscale anisotropy of the bioprinted microfibrous scaffold it can be possible to obtain engineered cardiac organoids characterized by improved alignment at the cellular level, mimicking the bundled structure of the myocardium in vivo. It should be noted that, the presence of crossing microfibers partially cancelled the macroscopic anisotropy of the overall structure. This effect nevertheless, could be minimized in bioprinted scaffolds with higher macroscale anisotropy (e.g., for those with a 2×5 ratio of the unit grids the microfibers aligning in the direction of the long axis were 2.5 times more than the perpendicular ones, thus still maintaining a relatively high degree of anisotropy), which further enhanced the alignment of the cardiomyocytes at the cellular level. Since scaffolds with an aspect ratio of unit grids of 2×5 presented better results in terms of the maturation, alignment, and contraction of the cardiomyocytes, they were chosen for all subsequent experiments involving heart-on-a-chip and cardiotoxicity studies.

3.3. Microfluidic Microbioreactor for On-Chip Integration of the Bioprinted Tissue Constructs

3.3.1. Bioreactor Design and Assembly

Referring again to FIG. 6A, an innovative resealable microbioreactor 60 for perfusion culture to support the long-term viability of the endothelialized myocardium and in situ observation of the bioprinted endothelialized myocardial constructs can be seen. As illustrated in FIG. 6A, the bioreactor 60 can be designed to possess two hemi-chambers embedded in a pair of PDMS gaskets 64a, 64b, which were sandwiched between two rigid supports 62a, 62b made of PMMA to ensure hydraulic tightness and fluidic integrity. The pair of micro-featured PDMS layers together formed the bioreactor chamber at a thickness of approximately 1 mm when closed together (which can further be reduced to approximately 0.85 mm upon compression), connected with the inlet and outlet channels on the two sides. The main chamber can be square (7×7 $mm^2$) with tapered edges 74. Turbulent or stagnation zones and bubble formation could be avoided in such a design due to the progressive increase and decrease of the cross-sectional area of the chamber, as well as the presence of rounded corners. A set of four PDMS micropillars (not shown in the Figures) can also be incorporated into the design of the central chamber of each bioreactor 60 to hold the scaffold 30 in place, avoiding its potential displacement during the perfused culture. Finally, the bioreactor 60 can be formed with a circular opening 76 in the center of one of the PMMA supports to enable direct microscopic monitoring of the beating behavior of the cardiac tissue construct, without the need of disassembling the bioreactor 60.

3.3.2. Computational Simulations

In the prior art, cardiomyocytes and endothelial cells are known to be sensitive to oxygen levels. A computational model was thus developed with the finite element method using COMSOL MULTI PHYSICS® to simulate the flow velocity in the bioreactor as well as oxygen distribution within and at the vicinity of the tissue construct. A flow rate of 50 μL/min can be adopted after scaling down the flow rate of the blood in the heart according to the weights of the heart and the engineered cardiac organoid. As indicated in the simulation results in FIG. 6C, the flow rates were uniform inside the chamber of the bioreactor except for slightly increased speed at the inlet/outlet and the corners where the pillars were present. More importantly, at such a perfusion rate of 50 μL/min, the oxygen concentrations across the volume of the scaffold were abundant. Indeed, even the center of the endothelialized myocardial construct could experience an oxygen level of approximately 0.12 mM, approximating the range required for optimal survival of cardiomyocytes and endothelial cells in engineered tissue constructs.

3.3.3. Effect of Perfusion on Cell Viability

Figure 6E:
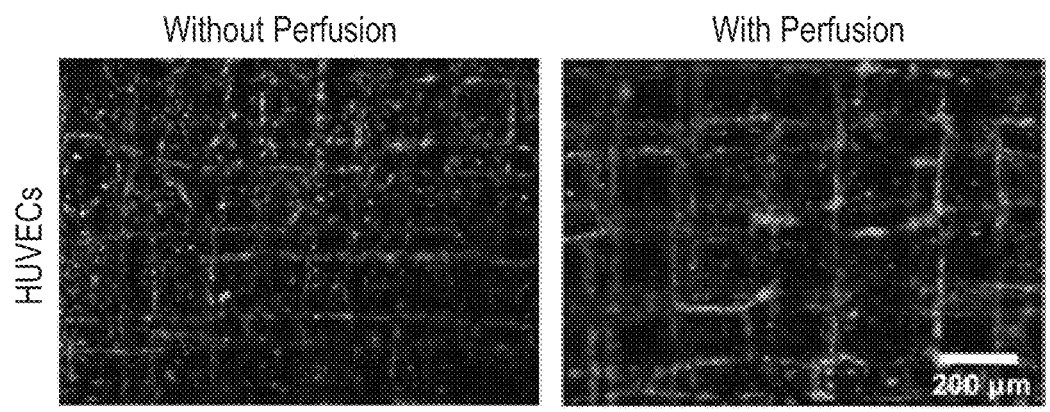
FIG. 6E can be a live/dead micrograph and quantified cell morbidity of bioprinted HUVECs in the endothelialized scaffold in the bioreactor of FIG. 6A without/with perfusion.
Figure 6F:
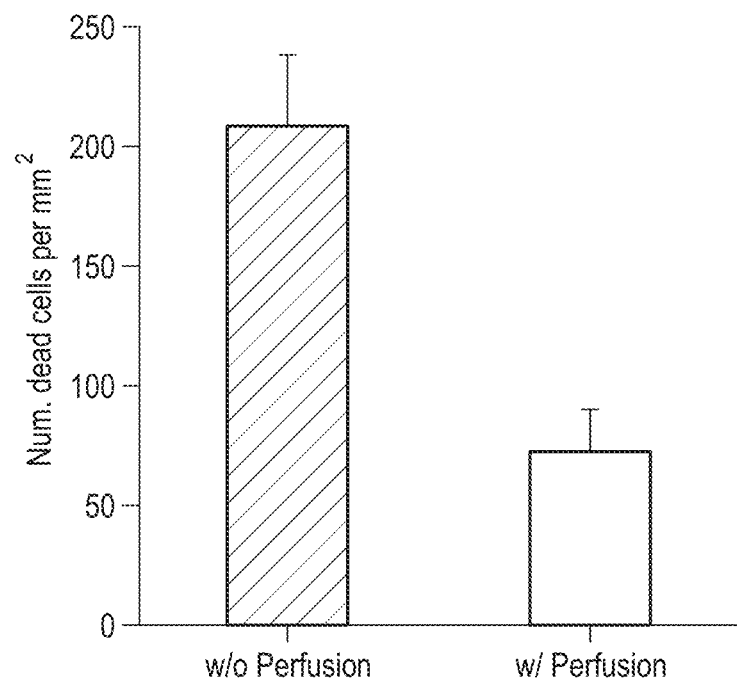
FIG. 6F can be a depiction of number of dead cells per $mm^2$ versus perfusion/no perfusion for the micrograph of FIG. 6E.
Figure 6G:
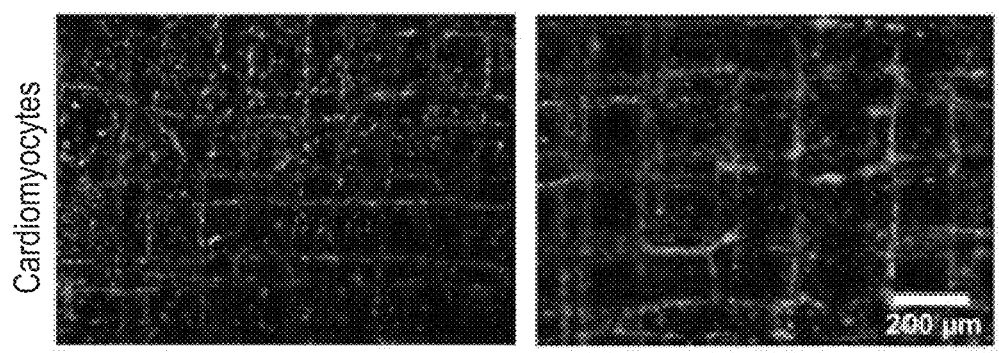
FIG. 6G can be a live/dead micrograph and quantified cell morbidity of bioprinted cardiomyocytes in the endothelialized scaffold in the bioreactor of FIG. 6A without/with perfusion.
Figure 6H:
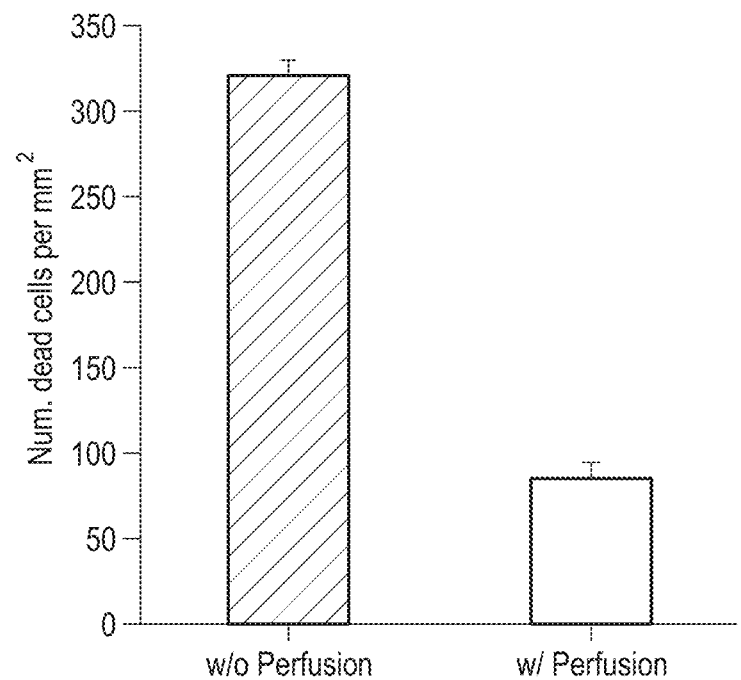
FIG. 6H can be a depiction of number of dead cells per minute versus perfusion/no perfusion for the micrograph of FIG. 6G.

The effects of perfusion of individual cell types were investigated. The tissue constructs were first cultured under static conditions for 3 days prior to being transferred to the bioreactors. The cell viability was then assessed using live/dead staining. The results of the assessment can be shown in FIG. 6E. In FIG. 6E, the HUVECs appear to have exhibited pronounced cellular mortality at Day 7 post culture in the bioreactor when no perfusion was applied with a large number of dead cells (red areas in FIG. 6E), whereas the viability of the cells was greatly improved when the scaffolds underwent perfusion culture at the flow rate of 50 µL The quantification result further revealed a significant difference between the two groups as shown by the histogram in FIG. 6F, for $p<0.001$). Similarly, the perfusion of the scaffolds during bioreactor culture also significantly reduced the total number of dead cardiomyocytes (FIG. 6G) as further depicted in a histogram (FIG. 6H, $p<0.05$). Consequently, we chose a perfusion rate of 50 µL/min for maintaining the bioprinted tissue constructs inside the bioreactor. It should be noted that the use of the microbioreactor 60 was not intended to simulate the flow patterns in the native myocardium; instead, the perfusion culture at the low flow rate could enhance the delivery of nutrients and oxygen to the embedded tissue constructs and support their long-term viability.

3.4. Endothelialized-Myocardium-on-a-Chip as an Enabling Cardiovascular Drug Screening Platform

3.4.1. Generation of Endothelialized-Myocardium-on-a-Chip Model

Thus far, the effects of bioink, scaffold architecture, and perfusion on the endothelialization and construction of cardiac tissues based on the bioprinted microfibrous scaffolds have been discussed. To implement these techniques according to some embodiments of the present invention, a preliminary study on neonatal rat cardiomyocytes seeded onto HUVECs-laden bioprinted scaffolds was performed. Since both HUVECs and cardiomyocytes were present, a 1:1 mixture of EGM and DMEM for the co-culture was employed. This common medium did not seem to pose any adverse influence on the viability and functionality of both cell types. In fact, the presence of vascular endothelial growth factor (VEGF), which is a standard supplement of the endothelial growth medium and further continuously secreted by the HUVECs in the vascular network, could on the contrary, enhance the cardiac function in engineered cardiac organoids through upregulation the Cx-43 expression as well as other contractile molecules.

Figure 7A:
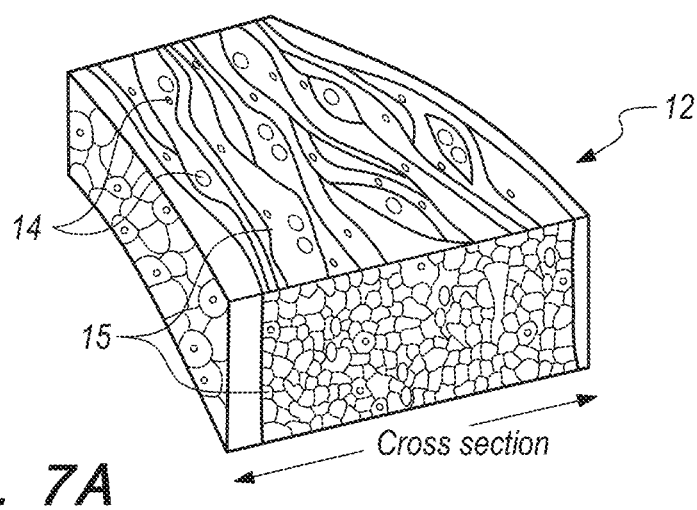
FIG. 7A can be a schematic showing a native myocardium containing blood vessels embedded in a matrix of cardiomyocytes.
Figure 7B:
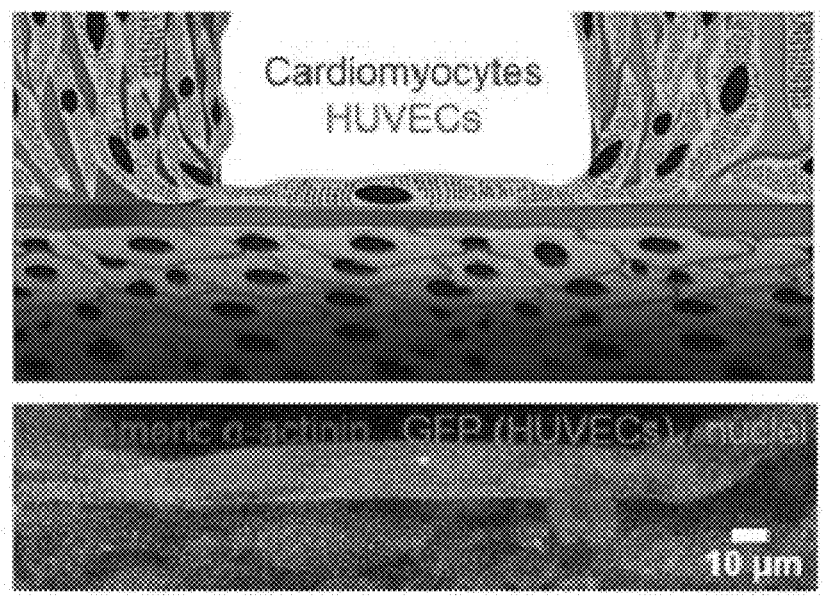
FIG. 7B can be a schematic and high-resolution confocal fluorescence micrograph showing an endothelialized myocardial tissue formed in accordance with the present invention, by seeding neonatal rat cardiomyocytes onto the bioprinted endothelialized microfibrous scaffold after 14 days of pre-endothelialization.

Referring now to FIG. 7A, a schematic of a native myocardium tissue 12 which has been bioprinted using the systems and methods according to several embodiments can be shown, where blood vessels 14 are embedded within a matrix of cardiomyocytes 15. From the schematic and magnified confocal fluorescence micrograph in FIG. 7B, it can be clear that the endothelial cells aligned at the periphery of the bioprinted microfiber, whereas the aligned cardiomyocytes tightly attached on the outside, together assuming the configuration of an endothelialized myocardial tissue resembling the structure of its native counterpart. It should be noted that, although in the current work these bioprinted endothelialized microfibers were not hollow, perfusion may be achieved in future designs, possibly by using sacrificial bioinks that can be later on removed are used during the bioprinting process. The endothelialized myocardial constructs exhibited uniform beating at a rate in the range of 50-70 bpm similar to monoculture, and the beating could extend to up to at least 2 weeks tested inside the bioreactor during perfusion culture.

Comparing to the existing engineered cardiac tissues, the bioprinting strategy as disclosed here can possess several advantages. More specifically, the size, shape, and architecture of the microfibrous scaffold can be conveniently controlled by programming the bioprinter. The ability to encapsulate endothelial cells that migrated and formed the lumen-like structure of the endothelium can further provide the opportunity to engineer co-cultured models of myocardial tissues with an organized network of endothelial cells, closely mimicking the structural arrangement and to a certain extent recapitulating the functionality of its in vivo counterpart.

To the best of the inventor's knowledge, the prior literature on the construction of 3D endothelialized myocardium for both regeneration and in the on-chip formats has focused on single cell type cultures and/or simplified co-cultures with limited structural similarity. In contrast, and most importantly, the systems and methods can employ a "platform technology", where the bioprinted microfibrous network emulating the blood vessels can serve not only as a vascular bed for myocardium, but also for engineering any type of endothelialized tissue besides the myocardium demonstrated in the Specification as disclosed herein.

3.4.2. Endothelialized-Myocardium-on-a-Chip for Cardiovascular Drug Testing Drug discovery can be a lengthy and expensive process. Accounting for organ side-effects has posed a great challenge for drug development and has resulted in rapidly increasing drug attrition rate. In particular, more than 15 drugs have been removed from the European and US markets over the past decade primarily due to toxicity concerns related with the cardiovascular system, contributing to half of the total drug retractions during this period of time. It can therefore be expected that the 3D endothelialized myocardium system fabricated using this innovative bioprinting technology as disclosed herein, when combined with physiological relevance through incorporation of the perfusable microfluidic bioreactor, will likely function to predict cardiovascular drug toxicity that could not be achieved using individual cell types alone.

Figure 7C:
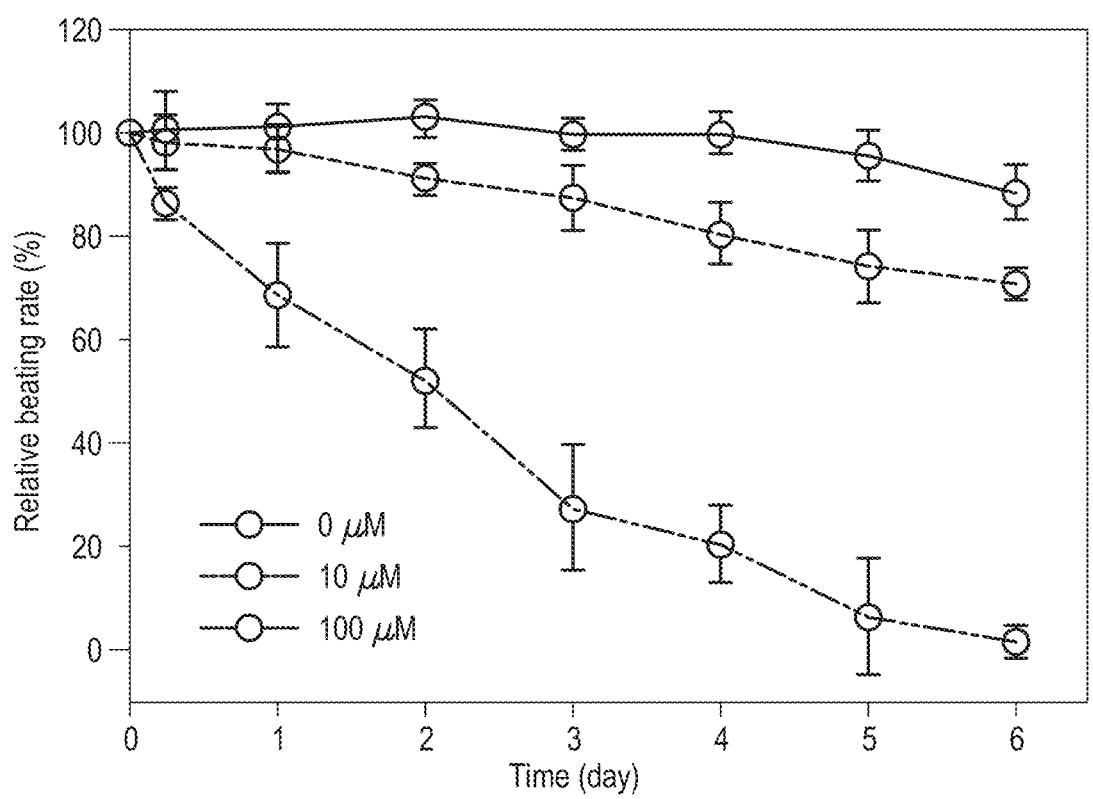
FIG. 7C can be a graph of relative beating of the endothelialized myocardial tissues versus time with different dosages of doxorubicin FIG. 7D can be a graph of relative change of levels of von Willebrand Factor (vWF) expression versus time with different dosages of doxorubicin.
Figure 7D:
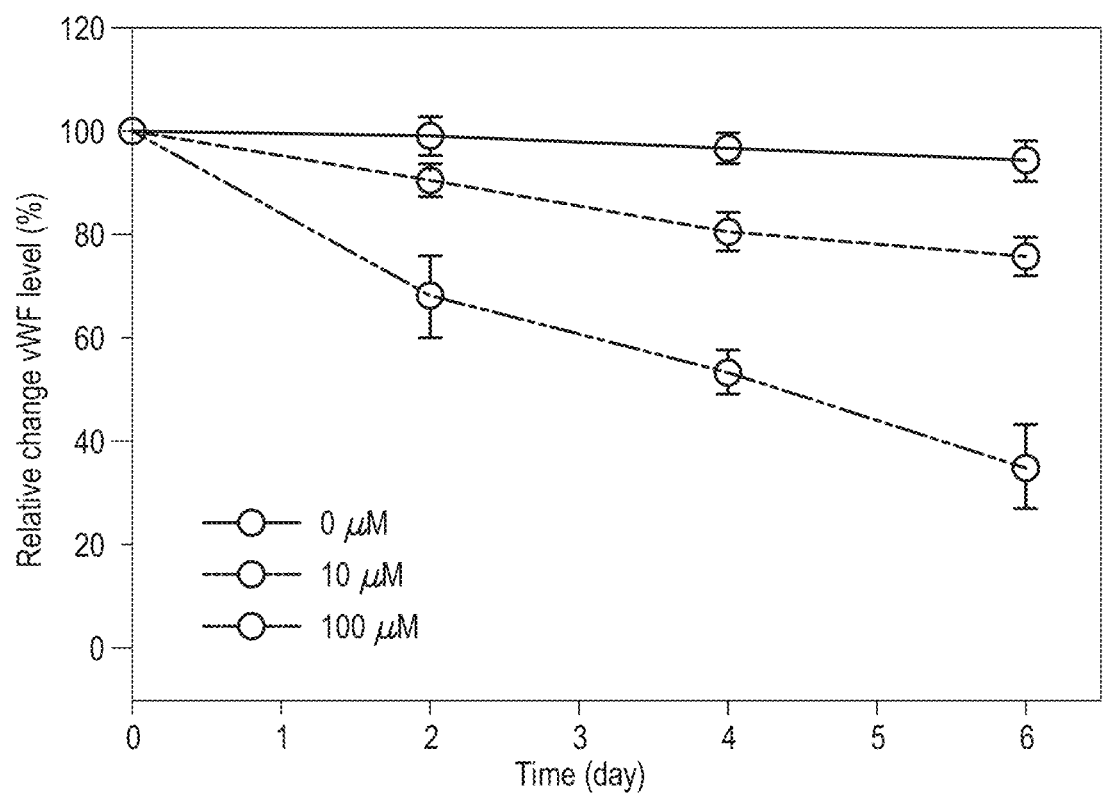

For example, the endothelialized-myocardium-on-a-chip model can be used to assess treatment by a common anticancer drug, doxorubicin. Unlike other pre-existing models, where only individual cell types were typically included, doxorubicin elicited dose-dependent responses towards both cardiomyocytes and endothelial cells when assessed using the systems and methods of several embodiments. For example, and as shown in FIG. 7C, the beating rate of the cardiomyocytes decreased to 70.5% and 1.62% (close to 0 bpm) at Day 6 post exposure to 10 µM and 100 µM drugs, respectively, while the control endothelialized myocardial organoids largely maintained a high relative beating rate at approximately 88.3%. This endurance towards doxorubicin of the cardiac tissues is comparable to prior art studies using two-dimensional (2D) monolayer cultures of cardiomyocytes, but with slight increment presumably due to the three-dimensionality of the model as well as the perfusion culture, both contributing to partially mitigated drug toxicity. Similarly, and as seen in FIG. 7D, the levels of von Willebrand factor (vWF) secreted by the endothelial cells also reduced to 76.0% and 35.3% at Day 6 for constructs treated with doxorubicin at 10 μM and 100 μM, respectively, while the levels for the controls remained at >90% at all of the time points tested and depicted in FIG. 7D.

3.4.3.
Endothelialized-Human-Myocardium-on-a-Chip: A Step Forward towards Personalized Medicine Prototype models have been optimized using neonatal rat cardiomyocytes due to their abundant availability as described above; however, it can also be demonstrated that the systems and methods can also include cardiomyocytes of human origin to construct an endothelialized-human-myocardium-on-a-chip model. In this case, hiPSC-cardiomyocytes were used as the source of cardiomyocytes. The hiPSCs represent a versatile cell source for obtaining a variety of mature cell types thanks to recent advancements on the prior art stem cell technology. These cells, obtainable from adult individuals can further open up the door towards personalized medicine for the potential in constructing patient-derived organoids. Prior studies have attempted to use hiPSC-cardiomyocytes and hiPSC-endothelial cells for investigating human cardiotoxicity caused by pharmaceutical compounds. However, only single cell types were analyzed individually in addition to the relatively simplified structures, when compared to our 3D bioprinted, endothelialized-human-myocardium-on-a-chip platform of the systems and methods of the present invention as reported in this Specification, when examining the ability of the structure to mimic its in vivo counterpart.

Figure 8A:
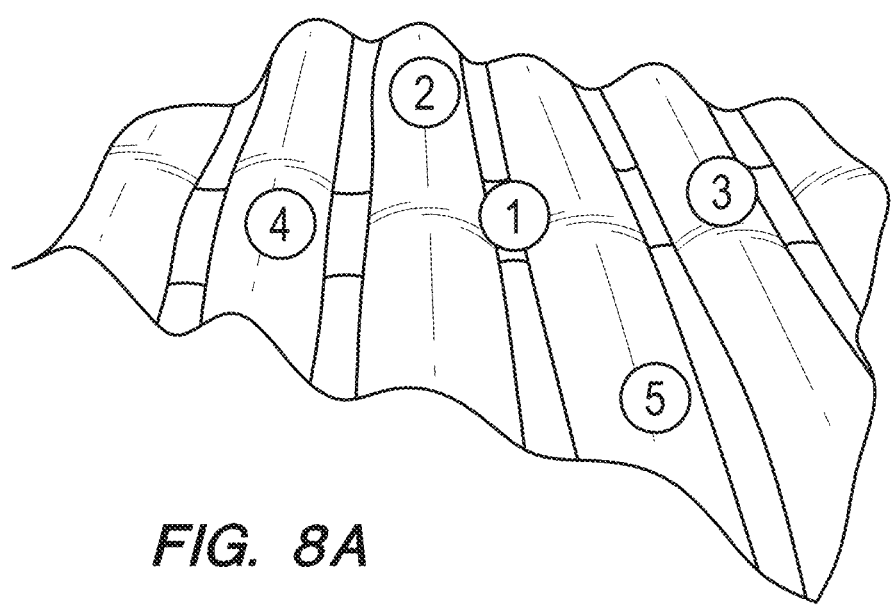
FIG. 8A can be a pseudo-3D brightfield micrograph showing an all-human endothelialized myocardial tissue formed by the methods according to several embodiments, by seeding hiPSC-derived cardiomyocytes onto the bioprinted endothelialized scaffold after 14 days of pre-endothelialization.
Figure 8B:
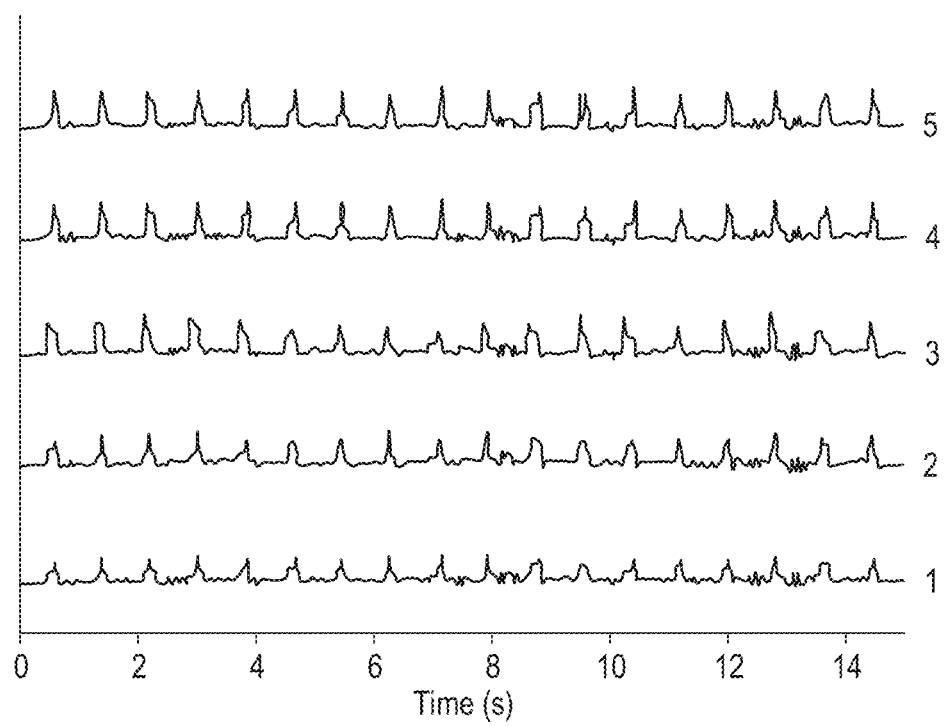
FIG. 8B can be a graph containing beating plots of the different local regions indicated in FIG. 8a, with the contraction amplitudes normalized to the same height for easy comparison across the samples.
Figure 8C:
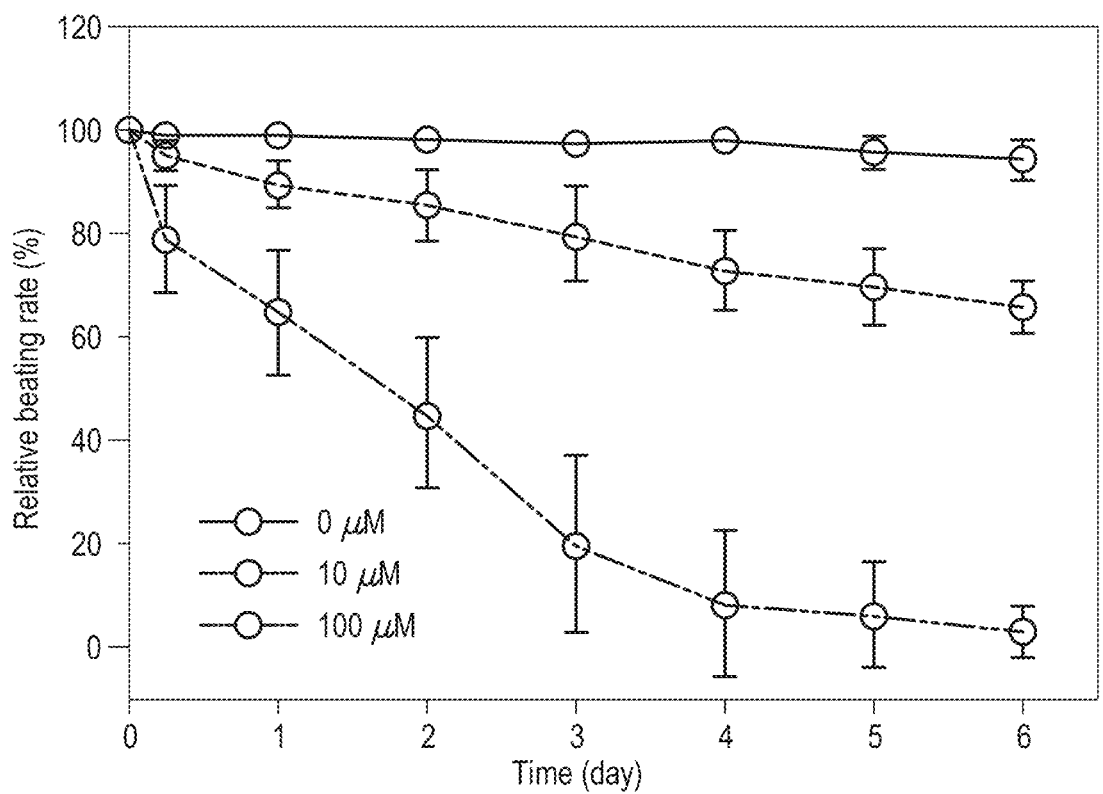
FIG. 8C can be a graph of relative beating of the endothelialized myocardial tissues by the endothelial cells upon treatment versus time with different dosages of doxorubicin for the tissue represented by FIG. 8A.
Figure 8D:
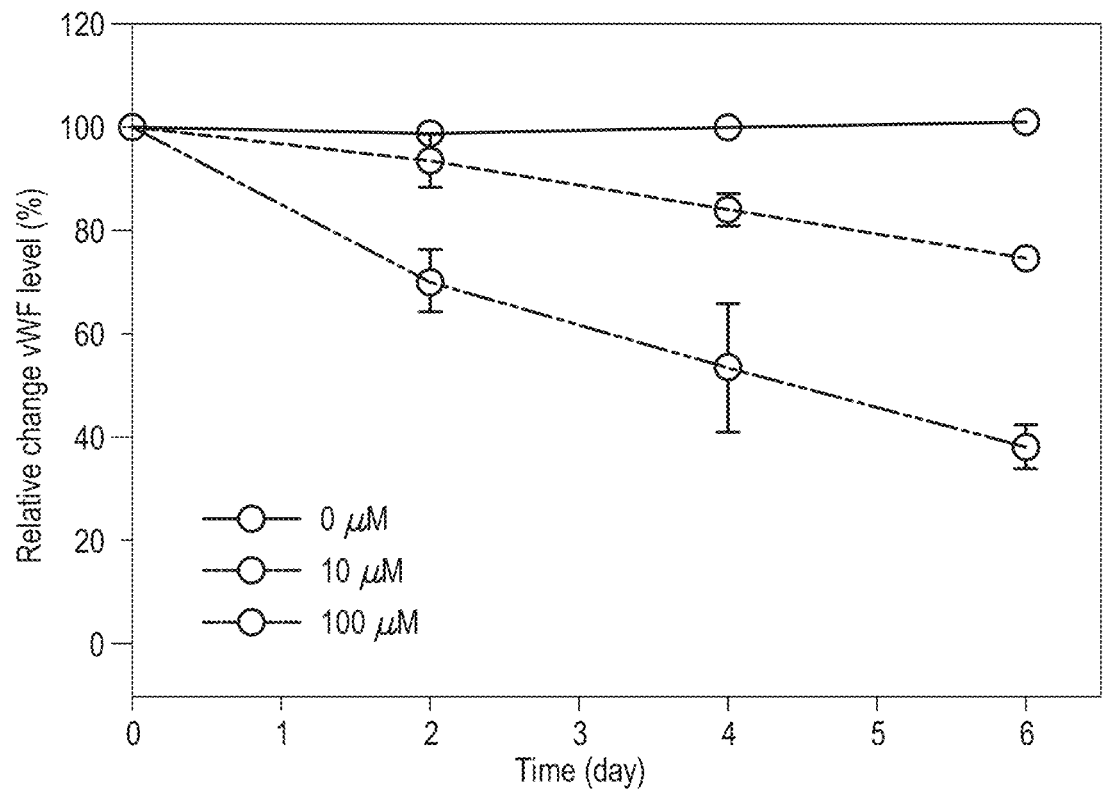
FIG. 8D can be a graph of relative change of levels of vWF expression versus time with different dosages of doxorubicin for the tissue represented by FIG. 8A; and, FIG. 9 can be a block diagram, which can be illustrative of steps that can be taken to accomplish some of the methods of the present invention according to several embodiments.

The same procedures for fabricating the vascular beds using bioprinted microfibrous scaffolds as described above were used, but hiPSC-cardiomyocytes were subsequently seeded instead of the neonatal rat cells. Similarly, a common medium composed of 1:1 mixture of EGM and RPMI/B27 (by GIBCO®) was adopted for the co-culture without imposing any adverse influence on both cell types. As expected, the resulting endothelialized human myocardial organoids presented uniform and highly synchronized beating across the entire scaffold 30 (Please see FIGS. 8A and 8B). The beating rate lasted at approximately 60 bpm for up to 7-10 days when cultured in the perfusion bioreactor 60, followed by slight decrease over the remaining period. In addition, both hiPSC-cardiomyocytes and endothelial cells showed dose-dependent responses towards doxorubicin. The beating of the hiPSC-cardiomyocytes reduced from 94.5% for the control constructs to 66.0% and 2.78% (close to 0 bpm) for those treated with 10 μM and 100 μM doxorubicin, respectively, as shown in FIG. 8C. The human-derived myocardial organoids seemed to have slightly lower endurance at all of the time points analyzed in comparison to those of rat origin (FIG. 8C versus FIG. 7C). By cross-referencing FIGS. 7D with 8D, the toxicity of doxorubicin on the endothelial component of the constructs at different doses corresponded well with that observed for the rat myocardial organoids due to the same origin of the cell source. Therefore, the endothelialized-myocardium-on-a-chip platform as disclosed herein can provide a model for probing drug-induced cardiovascular toxicity with a translational potential for personalized drug screening in the future.

Figure 9:
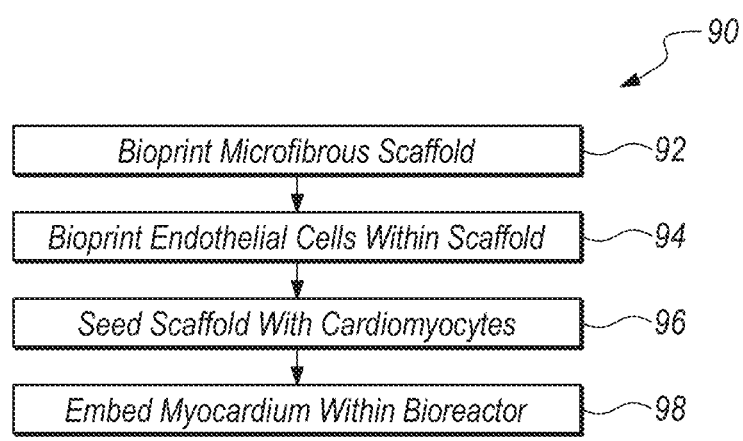

Referring briefly now to FIG. 9, a block diagram 90 is shown, which can be used to depict steps that can be taken to practice the methods of the present invention according to some embodiments. As shown method 90 can include the step 92 of 3D printing a microfibrous hydrogel scaffold and step 94 of bioprinting endothelial with the microfibrous scaffold 30. The methods can further include the step 96 of seeding the resulting scaffold with cardiomyocytes in a manner which results in functional tissue with a controlled anisotropy. The methods can optionally include the step of placing the scaffold 30 in a bioreactor 60 for perfusion. The manner and order of steps for the methods, and the materials used to accomplish the steps, are as described above.

4. Conclusions and Perspectives

In summary, a novel strategy to construct endothelialized-myocardial-tissues by adopting an innovative bioprinting technology has been presented herein. The endothelial cells, encapsulated inside the microfibers composing the backbone of the scaffolds, can gradually migrate towards the peripheries of the microfibers to form a layer of confluent endothelium. The assembly of the endothelial cells within the bioprinted microfibers can resemble a blood vessel structure, can be enabled by the composite bioink featuring a dual-step crosslinking procedure and can potentially be facilitated by the intrinsic polarization tendency of these cells and presence of a nutrient gradient across the diameter of the microfibers. Importantly, when combined with a microfluidic perfusion bioreactor, the endothelialized-myocardium-on-a-chip model could be used as a platform for cardiovascular drug screening, where dose-dependent responses of both cardiomyocytes and endothelial cells were observed. While the proof-of-concept optimizations were conducted using neonatal cardiomyocytes as a model cell type, it was also demonstrated that such systems might be conveniently translated to human cardiac organoids through the application of hiPSC-cardiomyocytes, although more detailed mechanisms on drug-induced cardiovascular toxicity still remain to be examined.

Still further, the combination of bioprinting, microfluidics, and stem cells in our endothelialized-myocardium-on-a-chip platform as described herein would provide an enabling technology for the development of next-generation human organ models for not only engineering healthy and diseased myocardial surrogates, but more importantly for their use in personalized drug screening to mitigate drug-induced cardiovascular toxicity or improve treatment efficacy. This endothelialized-myocardium-on-a-chip platform would also enable testing of nanomedicine (the application of nanotechnology to medicine), such as the interactions between nanoparticles and the cardiac cells as well as those between nanoparticles and the endothelium (e.g. nanoparticle-induced endothelial leakage, a non-toxic effect of nanoparticles on endothelial cells). It should be noted that, although the bioprinted microfibrous structures in this work were not perfusable, we anticipate the perfusion of such an endothelialized network in the future upon usage of sacrificial bioinks that can be removed, to enhance the biomimetic properties of produced vascularized organoids, which is currently under investigation and will be reported in our future reports.

The use of the terms "a" and "an" and "the" and similar references in the context of describing the invention (especially in the context of the following claims) is to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of the preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A bioreactor, comprising:
   a microfibrous hydrogel scaffold;
   said microfibrous hydrogel scaffold being made of a composite alginate-gelatin methacryloyl (GelMA) bio-ink and having endothelial cells directly embedded within said scaffold;
   said scaffold further being seeded with cardiomyocytes so that said bioreactor has a controlled anisotropy;
   said scaffold being placed in a chamber defined by two PDMS half pieces; and,
   said scaffold being in compression between said PDMS half pieces when said PDMS half pieces are fixed to each other.

2. The bioreactor of claim 1, wherein said hydrogel scaffold comprises a plurality of serpentine layers, having a primary axis defined by said serpentine layer, and further wherein successive said serpentine layers are placed on each other in a cross-hatch configuration, so that the primary axes of successive layers are perpendicular.

3. The bioreactor of claim 2, wherein said cross-hatch manner, establishes a plurality of rectangular holes, said rectangular holes having an aspect ratio when viewed in plan view.

4. The bioreactor of claim 3, wherein said aspect ratio is selected from the group consisting of 2×2, 2×3, 2×4, and 2×5.

5. The bioreactor of claim 3, wherein said successive layer that have a primary axis in the same direction are placed so that they are offset from each other.

6. The bioreactor of claim 1, wherein said cardiomyocytes are neonatal rat cardiomyocytes.

7. The bioreactor of claim 1, wherein said cardiomyocytes are human induced Pluripotent Stem Cell (hiPSC) cardiomyocytes.

8. The bioreactor of claim 1, wherein said microfibrous hydrogel scaffold is manufactured using additive manufacturing techniques.

9. A method for drug screening with the bioreactor of claim 1, the method comprising the steps of:
   A) additive manufacturing the microfibrous hydrogel scaffold;
   B) bioprinting the endothelial cells directly within said scaffold, said bioprinting step occurring concurrently with said step A);
   C) seeding the result of said step A) and said step B) with the cardiomyocytes to yield said myocardium, said step C) being accomplished with the controlled anisotropy; and
   D) screening said drug with the bioreactor.

10. The method of claim 9, further comprising the step of:
    E) embedding said myocardium from said step C) into the bioreactor that is a microfluidic perfusion bioreactor.

11. The method of claim 10, wherein said step C) is not accomplished until ten to fourteen days after the accomplishment of said step B).

12. The method of claim 10, wherein said step C) is accomplished with human-induced Pluripotent Stem Cell (hiPSC) cardiomyocytes.

13. The method of claim 12, wherein said hiPSC cardiomyocytes are specific to a patient being proposed for treatment, with said drug for which said method is being accomplished.

14. A method for fabricating endothelialized myocardium for use in the bioreactor of claim 8, the method comprising the steps of:
    A) additive manufacturing the microfibrous hydrogel scaffold;
    B) bioprinting the endothelial cells directly within said scaffold, said bioprinting step occurring concurrently with said step A);
    C) seeding the result of said step A) and said step B) with the cardiomyocytes to yield said myocardium; and,
    said step C) being accomplished with the controlled anisotropy.

15. The method of claim 14, further comprising the step of:
    D) embedding said myocardium from said step C) into the bioreactor that is a microfluidic perfusion bioreactor.

16. The method of claim 14, wherein said scaffold from step A) has a periphery, as further wherein said step C) is not accomplished until said endothelial cells from said step B) have migrated to said periphery.

17. The method of claim 16, wherein said step C) is not accomplished until ten to fourteen days after the accomplishment of said step B).

18. The method of claim 14, wherein said step C) is accomplished with neonatal rat cardiomyocytes.

19. The method of claim 14, wherein said step C) is accomplished with human-induced Pluripotent Stem Cell (hiPSC) cardiomyocytes.

20. The method of claim 14, wherein said step A) results in a scaffold having an aspect ratio selected from the group consisting of 2×2, 2×3, 2×4 and 2×5.

* * * * *